United States Patent
Hart et al.

(10) Patent No.: US 9,642,891 B2
(45) Date of Patent: May 9, 2017

(54) COMPOSITIONS AND METHODS FOR TREATING ROTATOR CUFF INJURIES

(75) Inventors: Charles E. Hart, Brentwood, TN (US);
Samuel E. Lynch, Franklin, TN (US);
Conan Young, Franklin, TN (US);
Joshua Nickols, Nashville, TN (US)

(73) Assignee: BioMimetic Therapeutics, LLC, Franklin, TN (US)

( * ) Notice: Subject to any disclaimer, the term of this patent is extended or adjusted under 35 U.S.C. 154(b) by 556 days.

(21) Appl. No.: 11/772,646

(22) Filed: Jul. 2, 2007

(65) Prior Publication Data

US 2008/0027470 A1    Jan. 31, 2008

Related U.S. Application Data

(60) Provisional application No. 60/817,874, filed on Jun. 30, 2006.

(51) Int. Cl.
*A61F 2/08*      (2006.01)
*A61K 38/18*    (2006.01)
*A61L 27/22*    (2006.01)

(52) U.S. Cl.
CPC ........ *A61K 38/1858* (2013.01); *A61L 27/227* (2013.01); *A61L 2430/10* (2013.01)

(58) Field of Classification Search
CPC .. A61K 2300/00; A61K 38/39; A61K 38/363; A61K 38/1875; A61K 38/014; A61K 35/12; A61K 38/1841
USPC ......... 623/13.11–13.2; 606/76–77, 214–218, 606/300–302, 304, 331
See application file for complete search history.

(56) References Cited

U.S. PATENT DOCUMENTS

| | | | |
|---|---|---|---|
| 3,943,072 A | | 3/1976 | Thomson et al. |
| 4,837,285 A | * | 6/1989 | Berg ........................ A61K 9/70 128/DIG. 8 |
| 4,845,075 A | | 7/1989 | Murray et al. |
| 4,861,757 A | | 8/1989 | Antoniades et al. |
| 4,874,746 A | | 10/1989 | Antoniades et al. |
| RE33,161 E | | 2/1990 | Brown et al. |
| 4,904,259 A | | 2/1990 | Itay |

(Continued)

FOREIGN PATENT DOCUMENTS

| | | |
|---|---|---|
| EP | 0 289 584 B1 | 11/1988 |
| EP | 0 479 799 B1 | 4/1992 |

(Continued)

OTHER PUBLICATIONS

Anitua et al.; "Autologous preparations rich in growth factors promote proliferation and induce VEGF and HGF production by human tendon cells in culture"; *Journal of Orthopaedic Research*, 23 (2005) 281-286.

(Continued)

*Primary Examiner* — Ann Schillinger
(74) *Attorney, Agent, or Firm* — Hilary Dorr Lang; Patterson Intellectual Property Law, PC

(57) ABSTRACT

The present invention provides compositions and methods for attaching tendon to bone. The present invention provides compositions and methods for treating rotator cuff injuries. In one embodiment, a method for treating rotator cuff injuries comprises providing a composition comprising PDGF disposed in a biocompatible matrix and applying the composition to at least one site of tendon reattachment on the humeral head.

37 Claims, 4 Drawing Sheets

(56) References Cited

U.S. PATENT DOCUMENTS

| | | | |
|---|---|---|---|
| 4,963,145 A | 10/1990 | Takagi et al. |
| 4,975,526 A | 12/1990 | Kuberasampath et al. |
| 5,011,910 A | 4/1991 | Marshall et al. |
| 5,013,649 A | 5/1991 | Wang et al. |
| 5,019,559 A | 5/1991 | Antoniades et al. |
| 5,034,375 A | 7/1991 | Antoniades et al. |
| 5,035,887 A | 7/1991 | Antoniades et al. |
| 5,045,633 A | 9/1991 | Murray et al. |
| 5,053,212 A | 10/1991 | Constantz et al. |
| 5,106,748 A | 4/1992 | Wozney et al. |
| 5,108,922 A | 4/1992 | Wang et al. |
| 5,112,354 A | 5/1992 | Sires |
| 5,116,738 A | 5/1992 | Wang et al. |
| 5,124,316 A | 6/1992 | Antoniades et al. |
| 5,128,321 A | 7/1992 | Murray et al. |
| 5,129,905 A | 7/1992 | Constantz |
| 5,141,905 A | 8/1992 | Rosen et al. |
| 5,149,691 A | 9/1992 | Rutherford |
| 5,165,938 A | 11/1992 | Knighton |
| 5,187,076 A | 2/1993 | Wozney et al. |
| 5,187,263 A | 2/1993 | Murray et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |
| 5,376,636 A | 12/1994 | Rutherford et al. |
| 5,457,093 A * | 10/1995 | Cini et al. ............... 514/12 |
| 5,460,962 A | 10/1995 | Kemp |
| 5,516,896 A | 5/1996 | Murray et al. |
| 5,518,680 A | 5/1996 | Cima et al. |
| 5,531,794 A | 7/1996 | Takagi et al. |
| 5,533,836 A | 7/1996 | Moore |
| 5,549,123 A | 8/1996 | Okuyama et al. |
| 5,599,558 A | 2/1997 | Gordinier et al. |
| 5,629,191 A | 5/1997 | Cahn |
| 5,635,372 A | 6/1997 | Celeste et al. |
| 5,650,176 A | 7/1997 | Lee et al. |
| 5,747,273 A | 5/1998 | Khosravi et al. |
| 5,759,815 A | 6/1998 | Charette et al. |
| 5,783,217 A | 7/1998 | Lee et al. |
| 5,804,176 A * | 9/1998 | Grotendorst ............... 424/85.1 |
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 | 8/2001 | Gordon |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 * | 3/2004 | Spector ............... 514/2 |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 | 9/2005 | Dalal et al. |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 | 3/2007 | Gilbertson et al. |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 | 1/2009 | Lynch |
| 7,491,384 B2 | 2/2009 | Hart et al. |
| 7,597,883 B2 | 10/2009 | Hart et al. |
| 7,799,754 B2 | 9/2010 | Hart et al. |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen et al. |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0127265 A1 | 9/2002 | Bowman et al. |
| 2002/0131989 A1 | 9/2002 | Brown et al. |
| 2002/0193883 A1 | 12/2002 | Wironen |
| 2003/0006025 A1 | 1/2003 | Manini et al. |
| 2003/0021827 A1 | 1/2003 | Malaviya et al. |
| 2003/0049328 A1 | 3/2003 | Dalal et al. |
| 2003/0055511 A1 | 3/2003 | Schryver et al. |
| 2003/0105015 A1 | 6/2003 | Gilbertson et al. |
| 2003/0109000 A1 * | 6/2003 | Moore et al. ............... 435/69.1 |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1 | 1/2004 | King et al. |
| 2004/0014727 A1 | 1/2004 | Garrett |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0059416 A1 | 3/2004 | Murray et al. |
| 2004/0064194 A1 | 4/2004 | Irie et al. |
| 2004/0076685 A1 | 4/2004 | Tas |
| 2004/0078077 A1 * | 4/2004 | Binette et al. ............... 623/13.17 |
| 2004/0078090 A1 | 4/2004 | Binette et al. |
| 2004/0197311 A1 | 10/2004 | Brekke et al. |
| 2004/0224027 A1 | 11/2004 | Spiro et al. |

(56) References Cited

U.S. PATENT DOCUMENTS

| | | | |
|---|---|---|---|
| 2004/0228870 A9 | 11/2004 | Hart et al. | |
| 2004/0230303 A1 | 11/2004 | Gomes et al. | |
| 2004/0243133 A1 | 12/2004 | Materna | |
| 2004/0265350 A1 | 12/2004 | Sambrook et al. | |
| 2005/0027367 A1 | 2/2005 | Heide et al. | |
| 2005/0031694 A1 | 2/2005 | Gilbertson et al. | |
| 2005/0074481 A1 | 4/2005 | Brekke et al. | |
| 2005/0098915 A1 | 5/2005 | Long et al. | |
| 2005/0107162 A1 | 5/2005 | Kilby et al. | |
| 2005/0107887 A1 | 5/2005 | Knothe Tate et al. | |
| 2005/0119754 A1 | 6/2005 | Trieu et al. | |
| 2005/0169893 A1 | 8/2005 | Koblish et al. | |
| 2005/0170012 A1 | 8/2005 | Dalal et al. | |
| 2005/0177203 A1 | 8/2005 | Brighton et al. | |
| 2005/0187162 A1 | 8/2005 | Dhanaraj et al. | |
| 2006/0029578 A1 | 2/2006 | Hoemann et al. | |
| 2006/0084602 A1 | 4/2006 | Lynch | |
| 2006/0149392 A1 | 7/2006 | Hsieh et al. | |
| 2006/0153816 A1* | 7/2006 | Brown et al. | 424/93.7 |
| 2006/0153817 A1 | 7/2006 | Kihm et al. | |
| 2006/0153818 A1 | 7/2006 | Dhanaraj et al. | |
| 2006/0154367 A1 | 7/2006 | Kihm et al. | |
| 2006/0177475 A1 | 8/2006 | Rueger et al. | |
| 2006/0190043 A1 | 8/2006 | Brighton et al. | |
| 2006/0198939 A1 | 9/2006 | Smith et al. | |
| 2006/0205652 A1 | 9/2006 | Zamora et al. | |
| 2006/0233853 A1 | 10/2006 | Remington et al. | |
| 2006/0246121 A1* | 11/2006 | Ma | A61K 9/0024 424/443 |
| 2006/0247156 A1 | 11/2006 | Vanderby et al. | |
| 2006/0287676 A1* | 12/2006 | Prajapati et al. | 606/228 |
| 2006/0292198 A1 | 12/2006 | Dalal et al. | |
| 2007/0003752 A1 | 1/2007 | Bruce et al. | |
| 2007/0026044 A1 | 2/2007 | Bunting et al. | |
| 2007/0048381 A1 | 3/2007 | Hart et al. | |
| 2007/0053951 A1 | 3/2007 | Gonzalez Santos et al. | |
| 2007/0129807 A1 | 6/2007 | Lynch et al. | |
| 2007/0160681 A1 | 7/2007 | Park et al. | |
| 2007/0190101 A1 | 8/2007 | Yang et al. | |
| 2007/0191851 A1 | 8/2007 | Ashammakhi | |
| 2007/0207185 A1 | 9/2007 | Hart et al. | |
| 2007/0218098 A1 | 9/2007 | Reif et al. | |
| 2007/0244484 A1 | 10/2007 | Luginbuehl | |
| 2007/0259018 A1 | 11/2007 | McKay | |
| 2007/0259814 A1 | 11/2007 | Lynch | |
| 2007/0260326 A1 | 11/2007 | Williams et al. | |
| 2007/0282455 A1 | 12/2007 | Luginbuehl et al. | |
| 2008/0317816 A1 | 12/2008 | Ma et al. | |
| 2009/0074753 A1 | 3/2009 | Lynch | |
| 2009/0092674 A1 | 4/2009 | Ingram et al. | |
| 2009/0130173 A1 | 5/2009 | Behnam et al. | |
| 2010/0136085 A1 | 6/2010 | Hart et al. | |
| 2010/0151025 A1 | 6/2010 | Lynch et al. | |
| 2010/0174368 A1 | 7/2010 | Lynch et al. | |
| 2010/0183515 A1 | 7/2010 | Hart et al. | |
| 2010/0196347 A1 | 8/2010 | Kery et al. | |
| 2010/0247651 A1 | 9/2010 | Kestler et al. | |

FOREIGN PATENT DOCUMENTS

| | | |
|---|---|---|
| EP | 0 530 804 A1 | 3/1993 |
| EP | 0 530 804 B1 | 3/1993 |
| EP | 0 741 785 B1 | 11/1996 |
| EP | 0 741 785 B2 | 11/1996 |
| EP | 0 896 825 A1 | 2/1999 |
| EP | 0 896 825 B1 | 2/1999 |
| EP | 0 994 694 B1 | 4/2000 |
| EP | 1 242 129 B1 | 6/2000 |
| EP | 1 025 871 A1 | 8/2000 |
| EP | 1 100 488 B1 | 5/2001 |
| EP | 1 146 897 B1 | 10/2001 |
| EP | 1 234 552 A1 | 8/2002 |
| EP | 1 234 552 B1 | 8/2002 |
| EP | 1 374 857 A1 | 1/2004 |
| EP | 1 410 811 A1 | 4/2004 |
| EP | 1 410 811 B1 | 4/2004 |
| EP | 1 464 307 A1 | 10/2004 |
| EP | 1 464 307 B1 | 10/2004 |
| EP | 1 561 481 A2 | 8/2005 |
| EP | 1 561 481 A3 | 8/2005 |
| EP | 1 563 846 A1 | 8/2005 |
| EP | 1 681 087 A2 | 7/2006 |
| EP | 1 681 087 A3 | 7/2006 |
| EP | 1 712 244 A1 | 10/2006 |
| EP | 1 719 531 A2 | 11/2006 |
| EP | 1 719 532 A2 | 11/2006 |
| GB | 2 367 497 A | 4/2002 |
| JP | 7-250688 A | 10/1995 |
| JP | 2003-265592 A | 9/2003 |
| WO | WO-88/03409 A1 | 5/1988 |
| WO | WO-91/15231 A1 | 10/1991 |
| WO | WO-91/18098 A1 | 11/1991 |
| WO | WO-92/09301 A1 | 6/1992 |
| WO | WO-92/16181 A2 | 10/1992 |
| WO | WO-93/00432 A1 | 1/1993 |
| WO | WO-93/05808 A1 | 4/1993 |
| WO | WO-93/08825 A1 | 5/1993 |
| WO | WO-93/09229 A1 | 5/1993 |
| WO | WO-93/16099 A2 | 8/1993 |
| WO | WO-93/20859 A1 | 10/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO-94/21681 A1 | 9/1994 |
| WO | WO-94/22463 A1 | 10/1994 |
| WO | WO-94/26892 A1 | 11/1994 |
| WO | WO-94/26893 A1 | 11/1994 |
| WO | WO-94/28889 A1 | 12/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/16035 A3 | 6/1995 |
| WO | WO-95/18856 A1 | 7/1995 |
| WO | WO-95/20967 A1 | 8/1995 |
| WO | WO 95/28124 | 10/1995 |
| WO | WO-95/28950 A1 | 11/1995 |
| WO | WO-96/01845 A1 | 1/1996 |
| WO | WO-96/02559 A1 | 2/1996 |
| WO | WO-96/13226 A1 | 5/1996 |
| WO | WO-96/16668 A1 | 6/1996 |
| WO | WO-96/17924 A2 | 6/1996 |
| WO | WO-96/17924 A3 | 6/1996 |
| WO | WO-97/13857 A1 | 4/1997 |
| WO | WO-98/00183 A2 | 1/1998 |
| WO | WO-98/00183 A3 | 1/1998 |
| WO | WO-98/40113 A1 | 9/1998 |
| WO | WO-98/41246 A2 | 9/1998 |
| WO | WO-98/41246 A3 | 9/1998 |
| WO | WO-98/51354 A2 | 11/1998 |
| WO | WO-98/51354 A3 | 11/1998 |
| WO | WO 99/30726 | 6/1999 |
| WO | WO-99/30726 A1 | 6/1999 |
| WO | WO-99/67289 A1 | 12/1999 |
| WO | WO-00/04940 A1 | 2/2000 |
| WO | WO-01/32197 A2 | 5/2001 |
| WO | WO-01/32197 A3 | 5/2001 |
| WO | WO-01/35932 A2 | 5/2001 |
| WO | WO-01/35932 A3 | 5/2001 |
| WO | WO-01/41822 A1 | 6/2001 |
| WO | WO-01/57083 A1 | 8/2001 |
| WO | WO-01/60424 A2 | 8/2001 |
| WO | WO-01/60424 A3 | 8/2001 |
| WO | WO-01/66044 A2 | 9/2001 |
| WO | WO-01/66044 A3 | 9/2001 |
| WO | WO 01/66130 A1 | 9/2001 |
| WO | WO-01/68135 A2 | 9/2001 |
| WO | WO-01/68135 A3 | 9/2001 |
| WO | WO-02/00244 A2 | 1/2002 |
| WO | WO-02/00244 A3 | 1/2002 |

(56) References Cited

FOREIGN PATENT DOCUMENTS

| | | |
|---|---|---|
| WO | WO-02/00272 A2 | 1/2002 |
| WO | WO-02/00272 A3 | 1/2002 |
| WO | WO0217795 | 3/2002 |
| WO | WO-02/36147 A1 | 5/2002 |
| WO | WO 02/062405 A2 | 8/2002 |
| WO | WO-02/067978 A1 | 9/2002 |
| WO | WO-02/070029 A2 | 9/2002 |
| WO | WO-02/070029 A3 | 9/2002 |
| WO | WO-02/102783 A1 | 12/2002 |
| WO | WO-03/006025 A1 | 1/2003 |
| WO | WO2006031196 | 3/2003 |
| WO | WO-03/043576 A2 | 5/2003 |
| WO | WO-03/043576 A3 | 5/2003 |
| WO | WO-03/065996 A2 | 8/2003 |
| WO | WO-03/065996 A3 | 8/2003 |
| WO | WO-03/070186 A2 | 8/2003 |
| WO | WO-03/070186 A3 | 8/2003 |
| WO | WO-03/071997 A1 | 9/2003 |
| WO | WO-2004/002539 A2 | 1/2004 |
| WO | WO-2004/002539 A3 | 1/2004 |
| WO | WO-2004/002539 C1 | 1/2004 |
| WO | WO-2004/010907 A1 | 2/2004 |
| WO | WO2004037094 | 5/2004 |
| WO | WO-2004/071543 A1 | 8/2004 |
| WO | WO-2004/073563 A2 | 9/2004 |
| WO | WO-2004/073563 A3 | 9/2004 |
| WO | WO-2004/110308 A2 | 12/2004 |
| WO | WO-2004/110308 A3 | 12/2004 |
| WO | WO-2004/110308 C2 | 12/2004 |
| WO | WO-2005/009496 A1 | 2/2005 |
| WO | WO-2005/032461 A2 | 4/2005 |
| WO | WO-2005/032461 A3 | 4/2005 |
| WO | WO-2005/042048 A2 | 5/2005 |
| WO | WO-2005/042048 A3 | 5/2005 |
| WO | WO 2005/046746 A2 | 5/2005 |
| WO | WO 2005/054279 A1 | 6/2005 |
| WO | WO-2005/072656 A1 | 8/2005 |
| WO | WO-2006/031388 A2 | 3/2006 |
| WO | WO-2006/031388 A3 | 3/2006 |
| WO | WO-2006/034365 A2 | 3/2006 |
| WO | WO-2006/034365 A3 | 3/2006 |
| WO | WO-2006/044334 A2 | 4/2006 |
| WO | WO-2006/044334 A3 | 4/2006 |
| WO | WO 2006/050493 A2 | 5/2006 |
| WO | WO-2006/093808 A1 | 9/2006 |
| WO | WO-2006/133403 A2 | 12/2006 |
| WO | WO-2006/133403 A3 | 12/2006 |
| WO | WO-2007/061889 A2 | 5/2007 |
| WO | WO-2007/061889 A3 | 5/2007 |
| WO | WO-2007/087436 A2 | 8/2007 |
| WO | WO-2007/087436 A3 | 8/2007 |
| WO | WO-2007/089997 A2 | 8/2007 |
| WO | WO-2007/089997 A3 | 8/2007 |
| WO | WO-2007/090102 A2 | 8/2007 |
| WO | WO-2007/090102 A3 | 8/2007 |
| WO | WO-2007/092622 A2 | 8/2007 |
| WO | WO-2007/092622 A3 | 8/2007 |
| WO | WO-2008/005427 A2 | 1/2008 |
| WO | WO-2008/005427 A3 | 1/2008 |
| WO | WO-2008/073628 A2 | 6/2008 |
| WO | WO-2008/073628 A3 | 6/2008 |
| WO | WO-2008/103690 A2 | 8/2008 |
| WO | WO-2008/103690 A3 | 8/2008 |
| WO | WO-2008/151193 A1 | 12/2008 |
| WO | WO-2010/030714 A2 | 3/2010 |
| WO | WO-2010/071857 A1 | 6/2010 |
| WO | WO-2010/102266 A1 | 9/2010 |

OTHER PUBLICATIONS

Duffy et al.; "Growth Factors and Canine Flexor Tendon Healing: Initial Studies in Uninjured and Repair Models"; *The Journal of Hand Surgery*; vol. 20A, No. 4, Jul. 1995, pp. 645-649.

Howell et al.; "Polypeptide growth factors for periodontal regeneration"; *Current Opinion in Periodontology* 1996, 3:149-156.

Hsu et al.; "Clinical Implications of Growth Factors in Flexor Tendon Would Healing"; *The Journal of Hand Surgery*; vol. 29A, No. 4, Jul. 2004, pp. 551-563.

Liang et al.; "Effect of cytokines on repair of tendon injury"; PubMed; Sep. 2000; 14(5):283-5.

Manske et al.; "Flexor Tendon Healing"; *Symposium on Flexor Tendon Surgery; Hand Clinics* vol. 1, No. 1, Feb. 1985; pp. 25-34.

Cho et al.; "Platelet-Derived Growth Factor—Modulated Guided Tissue Regenerative Therapy"; *J Periodontol*; Jun. 1995, vol. 66, No. 6, pp. 522-530.

Nakamura et al.; "Early biological effect of in vivo gene transfer of platelet-derived growth factor (PDGF)-B into healing patellar ligament"; *Gene Therapy* (1998) 5, 1165-1170.

Nevins et al.; "Periodontal Regeneration in Humans Using Recombinant Human Platelet-Derived Growth Factor-BB (rhPDGF-BB) and Allogenic Bone"; *J Periodontol*; Sep. 2003, vol. 74, No. 9, pp. 1282-1292.

Park et al..; "Periodontal Regeneration in Class III Furcation Defects of Beagle Dogs Using Guided Tissue Regenerative Therapy with Platelet-Derived Growth Factor"; *J Periodontol*, Jun. 1995, vol. 66, No. 6, pp. 462-477.

Rohrich et al.; "Mersilene Suture as a Vehicle for Delivery of Growth Factors in Tendon Repair"; *Journal of the American Society of Plastic Surgeons*; vol. 104(6), Nov. 1999, pp. 1713-1717.

Rutherford et al.; "Platelet-derived and insulin-like growth factors stimulate regeneration of periodontal attachment in monkeys"; *Journal of Periodontal Research*; 1992, vol. 27, Issue 4, Part 1, pp. 285-290.

Spindler et al.; "Patellar Tendon and Anterior Cruciate Ligament Have Different Mitogenic Responses to Platelet-Derived Growth Factor and Transforming Growth Factor β"; *Journal of Orthopaedic Research*; vol. 14, No. 4; 1996; pp. 542-546.

Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2F%2Fwww%2E7ware% . . . >, last visited on Feb. 24, 2010, 2 pages.

Adalberto et al. "Periodontal Regeneration," *J. Periodontal*, 2005, 76(9):1601-1622.

Adornato, M.C. et al. (Jul. 2007). "The Treatment of Bisphosphonate-Associated Osteonecrosis of the Jaws with Bone Resection and Autologous Platelet-Derived Growth Factors," *Journal of the American Dental Association* 138(7):971-977.

Aghaloo, T.L. DDS MD et al. "Evaluation of Platelet-Rich Plasma in Combination with Anorganic Bovine Bone in the Rabbit Cranium: A Pilot Study," *The International Journal of Oral and Maxillofaclal Implants*; 2004, 19:59-65.

Ahn, S-H. et al. (Jun. 2003). "Effect of Recombinant Human Bone Morphogenetic Protein-4 with Carriers in Rat Calvarial Defects," *Journal of Periodontology* 74(6):787-797.

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," *Tissue Eng.* 10(5/6):789-795.

Almojaly, S. (2008). "The Effect of Bisphosphonate, Alendronate, on Primary Human Alveolar Bone Cells," *Masters Abstracts International* 46(6):61.

American Dental Association (Jun. 2006). *Expert Panel Recommendations: Dental Management of Patients on Oral Bisphosphonate Therapy*, Report of the Council of Scientific Affairs, 14 pages.

Anitua, E. et al. "Autologous platelets as a source of proteins for healing and tissue regeneration," *Thromb Haemost*, 2004, 91:4-15.

Antoniades, H.N. et al. (May 27, 1983). "Human Platelet-Derived Growth Factor (PDGF): Amino-Terminal Amino Acid Sequence," *Science* 220:963-965.

Antoniades, H.N. et al. (1985). "Platelet-Derived Growth Factor: A Link to Malignant Transformation," in *Cancer Cells 3: Growth Factors and Transformations*, Fermasico, J. et al. eds., Cold Spring Harbor Laboratory: Cold Spring Harbor, NY, 3:145-151.

(56) References Cited

OTHER PUBLICATIONS

Anusaksathien et al. "Growth Factor Delivery to Re-Engineer Periodontal Tissues," *Current Pharmaceutical Biotechnology*, 2002, vol. 3(2):129-139.
Anusaksathien et al. "Platelet-Derived Growth Factor Gene Delivery Stimulates ex Vivo Gingival Repair," *Tissue Engineering*, 2003, 9(4):745-758.
Anusaksathien et al. "Effect of Sustained Gene Delivery of Platelet-Derived Growth Factor or Its Antagonist (PDGF—1308) on Tissue-Engineered Cementum," *J. Periodontal*, Mar. 2004, 75(3):429-440.
Arm, D.M. et al. "Effect of Controlled Release of Platelet-derived Growth Factor from a Porous Hydroxyapatite Implant on Bone Ingrowth," *Biomaterials*, 1996, 17(7):703-709.
Assael, L.A. (2006). "A Time for Perspective on Bisphosphonates," *J. Oral Maxillofac. Surg.* 64:87-879.
Babbush, C.A. DDS MSCD et al. "An In Vitro and In Vivo Evaluation of Autologous Platelet Concentrate in Oral Reconstruction," *Implant Dent.*, 2003, 12(1):24-34.
Barker, K. et al. (Jun. 2006). "Bisphosphonate-Associated Osteonecrosis of the Jaws: A Guide for the General Dental Practitioner," *Dental Update* pp. 270-275.
Basa, S. et al. (2004). "Alternative Bone Expansion Technique for Immediate Placement of Implants in the Edentulous Posterior Mandibular Ridge: A Clinical Report," *International Journal of Oral & Maxofacial Implants* 19(4):554-558.
Bateman, J. et al. "Platelet-Derived Growth Factor Enhancement of Two Alloplastic Bone Matrices," *J. Periodontol.* (Nov. 2005) 76(11):1833-1841.
Becker. W. et al. (Nov. 1992). "A Comparison of PTFE Membranes Alone or in Combination with Platelet-Derived Growth Factor and Insulin-Like Growth Factor-I, or Demineralized Freeze Dried Bone in Promoting Bone Formation Around Immediate Extraction Socket Implants: A Study in Dogs," *J. Periodtonol.* 63(11):929-940.
Berlemann, U. et al. (2002). "Adjacent Vertebral Failure After Vertebroplasty," *J. Bone Joint Surg. BR* 84(B):748-752.
Betsholtz, C. et al. (Apr. 24, 1986). "cDNA Sequence and Chromosomal Localization of Human Platelet-Derived Growth Factor A-Chain and its Expression in Tumour Cell Lines," *Nature* 320:695-699.
BioMimetic Therapeutics (Jun. 7, 2006). "BioMimetic Therapeutics Receives Approval to Market GEM 21S® Growth-Factor Enhanced Matrix in Canada," located at <http://www.biomimetics.com/cgi-bin/acuweb/acuweb.cgi?s=biom&t=NewsDetail.htm&StoryID=166&>, 5 pages.
BioMimetic Therapeutics (Feb. 21, 2007). "BioMimetic Therapeutics Recieves Orphan Drug Designation for rhPDGF-BB Treatment of Osteonecrosis of the Jaw," located at < http://biomimetics.com/cgi-bin/aw/acuweb.cgi?s=biomimetics&t=pressreleasedtl.htm&StoryID=112&>, last visited on Apr. 5, 2010, 6 pages.
Björkenheim, J.M. (1989). "Structure and Function of the Rabbit's Supraspinatus Muscle After Resection of its Tendon," *Acta Orthop. Scand.* 60(4):461-463.
Boileau, P. et al. (Jun. 2005). "Arthroscopic Repair of Full-Thickness Tears of the Supraspinatus: Does the Tendon Really Heal?" *J. Bone Joint Surg. Am.* 87-A(6):1229-1240.
Bolander, "Regulation of Fracture Repair by Growth Factors," *P.S.E.B.M.*, 1992, 200:165-170.
Bonfini, T. et al. (Jan. 1, 2006). "Autologous Marrow and Platel Gel in Bone Tissue Regeneration," *Cytotherapy* 8(1), Abstract No. 239, 2 pages.
Bora, F.W. Jr. et al. (Aug. 1987). "Joint Physiology, Cartilage Metabolism, and the Etiology of Osteoarthritis," *Hand Clin.* 3(3):325-336.
Boyden, E.M. et al. (Aug. 1995). "Late Versus Early Repair of Achilles Tendon Rupture: Clinical and Biomechanical Evaluation," *Clin. Orthop. Relat. Res.* 317:150-158.
Braddock, M. et al. (Oct. 2001). "Born Again Bone: Tissue Engineering for Bone Repair," *News Physiool. Sci.* 16:208-213.
Business Wire. (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at <http://www.highbeam.com/doc/1G1-68027113.html>, last visited on Apr. 26, 2010, 3 pages.
Camargo et al. "Platelet-rich Plasma and Bovine Porous Bone Mineral Combined with Guided Tissue Regeneration in the Treatment of Intrabony Defects in Humans," *J Periodont Res* 2002, 37:300-306.
Camargo, L.V. PM et al. "Effectiveness of a Combination of Platelet-Rich Plasma, Bovine Porous Bone Mineral and Guided Tissue Regeneration in the Treatment of Mandibular Grade II Molar Furcations in Humans," *J. Clin. Periodontol*, 2003, 30:746-751.
Camelo et al. "Clinical, radiographic, and histologic evaluation of human periodontal defects treated with bio-oss and bio-guide," *International Journal of Periodontics and Restorative Dentistry*, 1998, 18(4):321-332.
Camelo et al. "Periodontal regeneration with an autogenous bone-bio-oss composite graft and a bio-guide membrane," *International Journal of Periodontics and Restorative Dentistry*. 2001, 21(2):109-120.
Camelo, M. et al. (Nov. 3, 2003). "Periodontal Regeneration in Human Class II Furcations Using Purified Recombinant Human Platelet-Derived Growth Factor-BB (rhPDGF-BB) with Bone Allograft," *International Journal of Periodontics & Restorative Dentistry* 23(3):213-225.
Canalis, "Effect of Growth Factors on Bone Cell Replication and Differentiation," *Clinical Orthopedics and Related Research*, Mar. 1985, 193:246-263.
Catalano, L. et al. (2006). "Bisphoshonates and Risk of Osteonecorisis of the Jaws," *Haema* 9(3):410-414.
Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," *Acta Orthop. Scand.* 74(5):559-564.
Cenni, E. et al. (2005, e-pub. Feb. 1, 2005). "Plasma Levels of Platelet-Derived Growth Factor BB and Transforming Growth Factor in Patients with Failed Hip Protheses," *Acta Orthopaedica* 76(1):64-66.
Chen et al. "Adenoviral Gene Transfer of PDGF Downregulates Gas Gene Product PDGFR and Prolongs ERK and AktIPKB Activation," *Am J Physiol Cell Physiol.*, Mar. 2002, 282:C538-0544.
Chiandussi, S. et al. (2006). "Clinical and Diagnostic Imaging of Bisphosphonate-Associated Osteonecrosis of the Jaws," *Dentomaxillofacial Radiology* 35:236-243.
Chin, M. (1995). "Distraction Osteogenesis in Maxillofacial Surgery," Chapter 9 in *Tissue Engineering: Applications in Maxillofacial Surgery and Periodontics*, Lynch, S.E. et al. eds., Quintessence Publishing, pp. 147-159.
Clergeau, c.P. et al. (Feb. 1996). "Healing Response to Anorganic Bone Implantation in Periodontal Intrabony Defects in Dogs Part 1. Bone Regeneration. A Microradiographic Study," *J. Periodontool.* 67(2):140-149.
Cochran et al. "Effects of Platelet-Derived Growth Factor Isoforms on Calcium Release From Neonatal Mouse Calvariae," *Bone*, 1993, 14:53-58.
Collins, T. et al. (Aug. 22, 1985). "Cultured Human Endothelial Cells Express Platelet-Derived Growth Factor B Chain: cDNA Cloning and Structural Analysis," *Nature* 316:748-750.
Convery, F.R. et al. (Jan.-Feb. 1972). "The Repair of Large Osteochondral Defects. An Experimental Study in Horses," *Clin. Orthop. Relat. Res.* 82:253-262.
Cooke et al. "Effect of rhPDGR-BB Delivery on Mediators of Periodontal Wound Repair," *Tissue Engineering*, 2006, 12(6):1441-1450.
Cossolin, G.S.I. et al. ( Date Unknown) "Treatment of Avascular Osteonecrosis of the Jaws in Cancer Patients with a Histroy of Bisphosphonate Therapy by Combining Bone Resection and Autologous Platelet-Rich Plasma," *Hospital Santa Catarina* 10 pages.
Costa, M.A. et al. (Jul. 2006). "Tissue Engineering of Flexor Tendons: Optimization of Tenocyte Proliferation Using Growth Factor Supplementation," *Tissue Eng.* 12(7):1937-1943.
Courneya, J-P. et al. (2010). "Normal and Diseased Primary Human Tenocytes in Response to rhPDGF-BB," Poster No. 1118, $56^{th}$

(56) References Cited

OTHER PUBLICATIONS

*Annual Meeting of the Orhopaedic Research Society*, located at < http://www.ors.org/web/Transactions/56/1118.pdf>, last visited on Feb. 23, 2010, 1 page.
Curi et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," *Journal of Oral and Maxillofacial Surgery* 65(2):349-355.
Dalla-Favera, R. et al. (Nov. 12, 1982). "Chromosomal Localization of the Human Homolog (*c-sis*) of the Simian Sarcoma Virus *onc* Gene," *Science* 218:686-688.
Doolittle et al. (Jul. 15, 1983). "Simian Sarcoma Virus *onc* Gene *v-sis*, Is Derived from the Gene (or Genes) Encoding a Platelet-Derived Growth Factor," *Science* 221:275-277.
Dunn, C.A. et al. (Feb. 2005, e-pub. Nov. 6, 2004). "BMP Gene Delivery for Alveolar Bone Engineering at Dental Implant Defects," *Molecular Therapy* 11(2):294-299.
Easley, M.E. et al. (May 2000). "Isolated Subtalar Arthodesis," *JBJS* 82-A(5):613-624.
Eastell, R. et al. (Mar. 1991). "Classification of Vertebral Fractures," *J. Bone Miner. Res.* 6(3):207-215.
Fagan, M.C. et al. (2008). "Simultaneous Augmentation of Hard and Soft Tissues for Implant Site Preparation Using Recombinant Human Platelet-Derived Growth Factor: A Human Case Report," *Int. J. Periodontics Restorative Dent.* 28(1):37-43.
Farrugia, M.C. et al. (Jan. 2006). "Osteonecrosis of the Mandible or Maxilla Associated with the Use of New Generation Bisphosphonates," *The Laryngoscope* 116:115-120.
Feldman, D. et al. (Sep. 1998). "In a Time of Change, Orthopedics Sector is Marked by New Modalities," *The BBI Newsletter*, located at <http://findarticles.com/p/articles/mi_m3570/is_n9_v21/ai_n27541529>, last visited on Mar. 12, 2009, 2 pages.
Fennis et al. "Mandibular reconstruction: A clinical and radiographic animal study on the use of autogenous scaffolds and platelet-rich plasma," *Int. J. Oral Maxillofac. Surg.*, 2002, 31:281-286.
Fennis et al. "Mandibular reconstruction: A histological and histomorphometric study on the use of autoge-us scaffolds, particulate cortico-cancellous bone grafts and platelet rich plasma in goats," *Int. J. Oral Maxillofac. Surg.*, 2004, 33:48-55.
Ficarra, G. et al. (2005). "Osteonecrosis of the Jaws in Periodontal Patients with a History of Bisphophonates Treatment," *J. Clin. Periodontol.* 32:1123-1128.
Fontana et al. "Effect of Platelet-Rich Plasma on the Pert-implant Bone Response: An Experimental Study," *Implant Dentistry*, 2004, 13:73-78.
Fribourg, D. et al. (Oct. 15, 2004). "Incidence of Subsequent Vertebral Fracture After Kyphoplasty," *Spine* 29(20):2270-2276.
Fukui, A. et al. (Sep. 1993). "Isolation and Characterization of Xenopus activin and Follistatin," *Devel. Biol.* 159(1):131-139.
Galatz, L.M. et al. (Feb. 2004). "The Outcome and Repair Integrity of Completely Arthoscopically Repaired Large and Massive Rotator Cuff Tears," *J. Bone Joint Surg. Am.* 86-A(2):219-244.
Gamradt, S.C. et al. (Mar. 2007). "Platelet Rich Plasma in Rotator Cuff Repair," *Tech. In Orthop.* 22(1):26-33.
Garg, A.K. (1995). "Grafting Materials in Repair and Restoration," Chapter 5 in *Tissue Engineering: Applications in Maxillofacial Surgery and Periodontics*, Lynch, S.E. et al. eds., Quintessence Publishing, pp. 83-101.
Garg, "The Use of Platelet-Rich Plasma to Enhance the Success of Bone Grafts Around Dental Implants," *Dental Implantology Update*, Mar. 2000, 11(3):17-21.
Gazielly, D.F. et al. (Jul. 1994). "Functional and Anatomical Results After Rotator Cuff Repair," *Clin. Orthop. Relat. Res.* 304:43-53.
Gerber, C. et al. (May 1994). "Mechanical Strength of Repairs of the Rotator Cuff," *J. Bone Joint Surg. Br.* 76-B(3):371-380.
Gerber, C. et al. (Apr. 2000). "The Results of Repair of Massive Tears of the Rotator Cuff," *J. Bone Joint Surg. Am.* 82-A(4):505-515.
Giannobile et al. "Comparison of Canine and Non-Human Primate Animal Models for Periodontal Regenerative Therapy: Results Following a Single Administration of PDGF/IGF-I," *J. Periodontol.*, Dec. 1994, 65(12):1158-1168.
Giannobile, W.V. et al. (Jul. 1996). "Comparative Effects of Platelet-Derived Growth Factor and Insulin-Like Growth Factor-I, Individually and in Combination, on Periodontal Regeneration in *Macaca fascicularis*," *J. Periodontal Res.* 31(5):301-312.
Giannobile et al. "Periodontal Tissue Engineering by Growth Factors," *Bone*, Jul. 1996, 19(1), Supplement: 23S-37S.
Giannobile et al. "Non-Coordinate Control of Bone Formation Displayed by Growth Factor Combinations with IGF-I," *J Dent Res*, Sep. 1997, 76(9):1569-1578.
Giannobile et al. "Recombinant Human Osteogenic Protein-1 (OP-1) Stimulates Periodontal Wound Healing in Class III Furcation Defects," *J Periodontol*, Feb. 1998, 69(2):129-137.
Giannobile, "Platelet-Derived Growth Factor (PDGF) Gene Delivery for Application in Periodontal Tissue Engineering," *J Periodontol*, Jun. 2001, 72(6):815-823.
Gilbertson et al. "Platelet-derived Growth Factor C (PDGF-C), a Novel Growth Factor That Binds to PDGF α and β Receptor," *The Journal of Biological Chemistry*, Jul. 20, 2001, 276(29):27406-27414.
Goutalier, D. et al. (Jul. 1994). "Fatty Muscle Degeneration in Cuff Ruptures: Pre- and Postoperative Evaluation by CT Scan," *Clin. Orthop.* 304:78-83.
Grageda, "Platelet-Rich Plasma and Bone Graft Materials: A Review and a Standardized Research Protocol," *Implant Dentistry*, 2004, 13(4):301-309.
Green et al. "Immunolocalization of platelet-derived growth factor A and B chains and PDGF-α and β-receptors in human gingival wounds," *Journal of Periodontal Research*, 1997, 32(2):209-214.
Gronwald et al. "Cloning and expression of a cDNA coding for the human platelet-derived growth factor receptor: Evidence for more than one receptor class," *Proc. Natl. Acad. Sci. USA*, May 1988, 85:3435-3439.
Hanel, D.P. et al. (Jan. 2002). "Wrist Fractures," *Orthop. Clin. North Am.* 33(1):35-57.
Harryman, D.T. et al. (Aug. 1991). "Repairs of the Rotator Cuff," *J. Bone Joint Surg. Am.* 73-A(7):982-989.
Hart, C.E. et al. "Purification of PDGF-AB and PDGF-BB from Human Platelet Extracts and Identification of All Three PDGF Dimers in Human Platelets," *Biochemistry*, Jan. 9, 1990, 29(1):166-172.
Hart et al. "Synthesis, Phosphorylation, and Degredation of Multiple Forms of the Platelet-derived Growth Factor Receptor Studied Using a Mo-clonal Antibody," *The Journal of Biological Chemistry*, Aug. 5, 1987, 262 (22)10780-10785.
Hart et al. "Two Classes of PDGF Receptor Recognize Different Isoforms of PDGF," Science, Jun. 1988, 240:1529-1531.
Hattrup, S.J. et al. (1985). "A Review of Ruptures of the Achilles Tendon," *Foot & Ankle* 6(1):34-38.
Hee et al. (2003). "Do Autologous Growth Factors Enhance Transformational Lumbar Interbody Fusion?" *Eur. Spine. J.* 12(4):400-407.
Heini, P.F. et al. (2001, e-pub. Jun. 14, 2001). "Bone Substitutes in Vertebroplasty," *Eur. Spine J.* 10:S205-S213.
Helm et al. (Apr. 2001). "Bone Graft Substitutes for the Promotion of Spinal Arthrodesis," *Neurosur. Foc.* 10(4):1-5.
Higashi, T. et al. (Jun. 1996). "Influence of Particle Size of Calcium Phosphate Ceramics as a Capping Agent on the Formation of a Hard Tissue Barrier in Amputated Dental Pulp," *Journal of Endodontics* 22(6):281-283.
Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," *J. Orthopedic Res.* 26:83-90.
Hollinger, J.O. et al. (2008). "Therapeutic Opportunities for Bone Grafting," Chapter 68 in *Principles of Regenerative Medicine*, Atala, A. et al. eds., Academic Press: Burlington, MA, pp. 1164-1175.

(56) References Cited

OTHER PUBLICATIONS

Hossain, M.Z. et al. (Jul. 1996). "Biological Responses of Autogenous Bone and Beta-Tricalcium Phosphate Ceramics Transplanted into Bone Defects to Orthodontic Forces," *Cleft Palate—Craniofacial Journal* 33(4):277-283.

Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," *J. Periodontol.*, Dec. 1997, 68(12):1186-1193.

Howes et al. "Platelet-Derived Growth Factor Enhances Demineralized Bone Matrix-Induced Cartilage and Bone Formation," *Calcif Tissue Int.*, 1988, 42:34-38.

Huang, L-H. et al. "The Effect of Platelet-Rich Plasma on the Coronally Advanced Flap Root Coverage Procedure: A Pilot Human Trial," J. Periodontal, Oct. 2005, 76(10):1768-1777.

Ikezawa et al. "Characterization of Cementum Derived Growth Factor as an Insulin-Like Growth Factor-I Like Molecule," *Connective Tissue Research*, 1997, 36(4):309-319.

Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," *J. Biomed. Mater. Res.* 69A:454-461.

Jensen et al. "Platelet rich plasma and fresh frozen bone allograft as enhancement of implant fixation—An experimental study in dogs," *Journal of Orthopaedic Research*, 2004, 22:653-658.

Jiang, D. et al. "Modification of an Osteoconductive Anorganic Bovine Bone Miami Matrix with Growth Factors," *J. Periodonlol.*, Aug. 1999, 70(8):834-839.

Jin et al. "Engineering of Tooth-Supporting Structures by Delivery of PDGF Gene Therapy Vectors," *Molecular Therapy*, Apr. 2004, 9(4):519-526.

Jin, Q. et al. (Mar. 5, 2008). "Nanofibrous Scaffolds Incorporating PDGF-BB Microspheres Induce Chemokine Expression and Tissue Neogenesis In Vivo," *PLoS One* 3(3):e1729, pp. 1-9.

Jones et al. (1992). "Isolation of Vgr-2, a Novel Member of the Transforming Growth Factor-Beta-related Gene Family," *Mol Endocnnol.* 6(11):1961-1968.

Jozsa, L. et al. (Aug. 1989). "Fibronectin and Laminin in Achilles Tendon," *Acta Orthop Sacninavica* 60(4):469-471.

Kademani, D. et al. (Aug. 2006). "Primary Surgical Therapy for Osteonecrosis of the Jaw Secondary to Bisphosphonate Therapy," *Mayo Clin. Proc.* 81(8):1100-1103.

Kaigler, "Growth factor delivery for oral and periodontal tissue engineering," *Expert Opin Drug Deliv.*, 2006, 3(5):647-662.

Kapuściński, P. et al. (Jul.-Sep. 1996). "An Analgesic Effect of Synthetic Human Calcitonin in Patients with Primary Osteoporosis," *The Polish Journal of Medicine and Pharmacy* 28(98):83-86.

Kassolis et al. "Alveolar Ridge and Sinus Augmentation Utilizing Platelet-Rich Plasma in Combination with Freeze-Dried Bone Allograft: Case Series," *Journal of Periodontology*, Oct. 2000, 71(10):1654-1661.

Kazlauskas et al. "Different effects of homo- and heterodimers of platelet-derived growth factor A and 8 chains on human and mouse fibroblasts," *The EMBO Journal* (1988) 7 (12):3727-3735.

Kim et al. "A Comparative Study of Osseointegration of Avana Implants in a Demineralized Freeze-Dried Bone Alone or With Platelet-Rich Plasma," *J Oral Maxillofac Surg*, 2002, 60:1018-1025.

Kim et al. "Use of Particulate Dentin-Plaster of Paris Combination with/without Platelet-Rich Plasma in the Treatment of Bone Defects Around Implants," *The International Journal of Oral & Maxillofacial Implants*, 2002; 17:86-94.

Klotzbuecher, C.M. et al. (Apr. 2000). "Patients with Prior Fractures Have an Increased Risk of Future Fractures: A Summary of the Literature and Statistical Synthesis," *J. Bone Miner. Res.* 15(4):721-739.

Kovacevic, D. et al. (Mar. 2008). "Biological Augmentation of Rotator Cuff Tendon Repair," *Clin. Orthop. Relat. Res.* 466(3):622-633.

Kovacs et al. "Comparative Study of b-Tricalclum Phosphate Mixed with Platelet-Rich Plasma versus β-Tricalcium Phosphate, A Bone Substitute Material in Dentistry," *Acts Veterinaria Hungarica*, 2003, 51(4):475-484.

Landesberg et al. "Quantification of Growth Factor Levels Using a Simplified Method of Platelet-Rich Plasma Gel Preparation," *J. Oral Maxillofac. Surg.*, 2000, 58:297-301.

Lasa et al. "Delivery of Demineralized Bone Powder by Fibrin Sealant," *Plast. Reconstr. Surg.*, 1995, 96(6):1409-1417.

Lasa Jr., C. et al. (1996). "Bone Induction by Demineralized Bone Powder and Partially Purified Osteogenin Using a Fibrin-Sealant Carrier," Chapter 14 in *Surgical Adhesives and Sealants: Current Technology and Applications*, Sierra, D. et al. eds., Technomic Publishing Company, Inc.: Lancaster, PA, pp. 135-144.

Lee et al. "The bone regenerative effect of platelet-derived growth factor-BB delivered with a chitosan/tricalcium phosphate sponge carrier," *J. Periodontal.*, 2000, 71(3):418-424, Abstract Only.

Lee, S.J. et al. (2001, e-pub. Feb. 13, 2001). "Molded Porous Poly ($_L$-Lactide) Membranes for Guided Bone Regeneration with Enhanced Effects by Controlled Growth Factor Release," *Journal of Biomedical Materials Research* 55:295-303.

Lee et al. "Enhanced bone formation by controlled growth factor delivery from chitosan-based biomaterials," *Journal of Controlled Release*, 2002, 78: 187-197.

Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," *J. Periodontol.* 73(2):198-205.

Letson, A.K. et al. (1994). "The Effect of Combinations of Growth Factors on Ligament Healing," *Clinical Orhopaedics and Related Research* 308:207-212.

Lind et al. (1998). "Growth Factor Stimulation of Bone Healing," *Acta Orthopaedica Scandinavica Supplementum* Suppl. 283:2-37.

Lioubavina-Hack et al. "Methyl cellulose gel obstructed bone formation by GBR: an experimental study in rats," *J. Clin. Periodontol.*, 2005, 32:1247-1253.

Lioubavina-Hack et al. "Effect of Bio-Oss® with or without platelet-derived growth factor on bone formation by 'guided tissue regeneration': a pilot study in rats," *J Clin. Periodontol*, 2005, 32(12):1254-1260.

Lipshitz, H. et al. (Jun. 1975). "In Vitro Wear of Cartilage," *J. Bone Joint Surg. Am.* 57A(4):527-534.

Lynch, S.E. et al. (Nov. 1987). "Role of Platelet-Derived Growth Factor in Wound Healing: Synergistic Effects with Other Growth Factors," *Proc. Natl. Acad. Sci. USA* 84:7696-7700.

Lynch, S.E. et al. (1989). "A Combination of Platelet-Derived and Insulin-Like Growth Factors Enhances Periodontal Regeneration," *J. Clin. Periodontol.* 16:545-548.

Lynch, S.E. (1990). "A Possible Role for Polypeptide Growth and Differentiation Factors in Periodontal Regeneration," *Executive Committee on Chemotherpeutics; Amer. Acad Peridontal—Position Paper* pp. 1-5.

Lynch, S.E. et al. (Jul. 1991). "The Effects of Short Term Application of a Combination of Platelet-Derived and Insulin-Like Growth Factors on Periodontal Wound Healing," *J. Periodontol.* 62(7):458-467.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," *J. Periodontol.* 62(11):710-717.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," *Wound Rep. Reg.* 2(3):182-190.

Lynch, S.E. (1995). "Introduction," in *Tissue Engineering: Applications in Maxillofacial Surgery and Preiodontics*, Lynch, S.E. et al. eds., Quintessence Publishing, pp. xi-xvi.

Lynch, S.E. (2005). "Bone Regeneration Techniques in the Orofacial Region," Chapter 18 in *Bone Regeneration and Repair: Biology and Clinical Applications*, Lieberman, J.R. et al. eds., Humana Press Inc.: Totowa, NJ, pp. 359-390.

(56) References Cited

OTHER PUBLICATIONS

Lynch, S.E. et al. (Dec. 2006). "A New Era in Periodontal and Periimplant Regeneration: *Use of Growth-Factor Enhanced Matrices Incorporating rhPDGF*," Compendium of Continuing Education in Dentistry 27(12):672-679.

Maiorana et al. "Maxillary Sinus Augmentation with Anorganic Bovine Bone (Bio-Oss) and Autologous Platelet-Rich Plasma: Preliminary Clinical and Histologic Evaluations," *Int J Periodontics Restorative Den*, 2003, 23(3):227-235.

Marcopoulou et al. (2003). "Proliferative Effect of Growth Factors TGF-β1, PDGF-BB, and rhBMP-2 on Human Gingival Fibroblasts and Periodontal Ligament Cells," *Journal of International Academy of Periodontology* 5(3):63-70.

Marx, R.E. et al. (2005). "Bisphosphonate-Induced Exposed Bone (Osteonecrosis/Osteoperosis) of the Jaws: Risk Factors, Recognition, Prevention, and Treatment," *J. Oral Maxillofac. Surg.* 63:1567-1575.

Mayfield, L. et al. (Oct. 1998). "Clinical and Radiographic Evaluation, Following Delivery of Fixed Reconstructions, at GBR Treated Titanium Fixtures," *Clin. Oral Implants Res.* 9:292-302.

McAllister et al. "Eighteen-month Radiographic and Histologic Evaluation of Sinus Grafting with A-rganic Bovine Bone in the Chimpanzee," *The International Journal of Oral & Maxillofacial Implants*, 1999, 14(3):361-368.

McGuire, M.K. et al. (2006). "rhPDGF-BB Promotes Healing of Periodontal Defects: 24-Month Clinical and Radiographic Observations," *Int. J. Periodontics Restorative Dent.* 26(3):223-231.

McMurty, R.Y. et al. (1992). "Fractures of the Distal Radius," Chapter 35 in *Skeletal Trauma*, Browner B.D. et al. eds., W.B. Saunders Company: Philadelphia, PA, 2:1063-1094.

Melo, M.D. et al. (Dec. 2005). "Osteonecrosis of the Jaws in Patients with a History of Receiving Bisphosphonate Therapy. Strategies for Prevention and Early Recognition," *J. American Dental Association* 136:16751681.

Migliorati, C.A. et al. (Jun. 2006). "Bisphosphate-Associated Osteonecrosis: A Long Term Complication of Bisphophonate Treatment," *Lancet Oncol.* 7:508-514.

Mitlak et al. "The Effect of Systemically Administered PDGF-BB on the Rodent Skeleton," *Journal of Bone and Mineral Research*, 1996, 11(2):238-247.

Molloy, T. et al. (2003). "The Roles of Growth Factors in Tendon and Ligament Healing," *Sports Med.* 33(5):381-394.

Mont, M.A. et al. (Oct. 1998). "Osteonecrosis of the Femoral Head. Potential Treatment with Growth and Differentiation Factors," *Clin. Orthop. Relat. Res.* 355(Suppl.):S314-S335, Abstract Only, 2 pages.

Morris, G.J. et al. (Jan. 2007). "Bisphosphonate Therapy for Women with Breast Cancer and at High Risk for Osteoporosis," *Journal of the National Medical Association* 99(1):35-45.

Mott, D.A. et al. (2002). "Enhancement of Osteoblast Proliferation in vitro by Selective Enrichment of Demineralized Freeze-Dried Bone Allograft with Specific Growth Factors," *J. Oral Implantol.* 28(2):57-66.

Mumford, J.H. et al. (Mar. 2001). "The Effects of Platelet Derived Growth Factor-BB on Periodontal Cells in In Vitro Wound Model," *J. Periodontal.* 72(3):331-340.

Nancollas, G.H. et al. (2006, e-pub. Jul. 2005). "Novel Insights into Actions of Bisphosphonates on Bone: Differences in Interactions with Hydrozyapatite," *Bone* 38:617-627.

Nase, J.B. et al. (Aug. 2006). "Osteonecrosis of the Jaw and Oral Bisphosphonate Treatment," *J. American Dental Association* 137:1115-1119.

Nash, T.J. et al. (Mar. 1994). "Effect of Platelet-Derived Growth Factor on Tibial Osteotomies in Rabbits," *Bone* 15(2):203-208.

Nevins, M.L. et al. (2003). "Evaluation of Periodontal Regeneration Following Grafting Intrabony Defects with Bio-Oss® Collagen: A Human Histologic Report," *Int. J. Periodont. Rest. Dent.* 23(1):9-17.

Nevins, M. et al. (2007). "Clinical Results Using Recombinant Human Platelet-Derived Growth Factor and Mineralized Freeze-Dried Bone Allograft in Periodontal Defects," *Int. J. Periodontics Restorative Dent.* 27(5):421-427.

Nociti, F.H. Jr. et al. (2000). "Histometric Evaluation of Bone Regeneration Around Immediate Implants Partially in Contact with Bone: A Pilot Study in Dogs," *Implant Dentistry* 9(4):321-328.

Orbay, J.L. et al. (Jan. 2004). "Volar Fixed-Angle Plate Fixation for Unstable Distal Radius Fractures in the Elderly Patient," *J. Hand Surg.* 29A(1):96-102.

Orthovita, Inc. (Dec. 14, 2000). "510(k) Summary. Vitoss™ Scaffold Syntehtic Cancellous Bone Void Filler," located at <http://www.accessdata.fda.gov/cdrh_docs/pdf/k994337.pdf>, last visited on Mar. 30, 2010, 6 pages.

Owen et al. (1984). "Simian Sarcoma Virus-Transformed Cells Secrete a Mitogen Identical to Platelet-Derived Growth factor," *Science* 25:54-56.

Palti, A. et al. (2002). "A Concept for the Treatment of Various Dental Bone Defects," *Implant Dentistry* 11(1):73-78.

Parashis, A. et al. (Jul. 1998). "Comparison of 2 Regenerative Procedures—Guided Tissue Regeneration and Demineralized Freeze-Dried Bone Allograft—in the Treatment of lntrabony Defects: A Clinical and Radiographic Study," *J. Periodontol.* 69(7):751-758.

Paul, W. et al. (1999). "Development of Porous Spherical Hydroxyapatite Granules: Application Towards Protein Delivery," *J. Mater. Sci. Mater. Med.* 10:383-388.

Persson, G.R. et al. (2000). "A Retrospective Radiographic Outcome Assessment Study of Intra-Bony Defects Treated by Osseous Surgery or by Bone Graft Procedures," *J. Clin. Periodontol.* 27:104-108.

Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts,"*Arch. Orthop. Trauma Surg.* 123(9):485-488.

Pfeilschifter, J. et al. (Jul.-Dec. 1990). "Stimulation of Bone Matrix Apposition in Vitro by Local Growth Factors: A Comparison Between Insulin-Like Growth Factor I, Platelet Derived Growth Factor, and Transforming Growth Factor β," *Endocrinology* 127(1):69-75.

Philippart et al. "Human Recombinant Tissue Factor, Platelet-rich Plasma, and Tetracycline Induce a High-Quality Human Bone Graft a 5-year Survey," *The International Journal of Oral and Maxillofacial Implants*, 2003, 18(3):411-416.

Phillips, S. et al. (1988). "The Direct Medical Costs of Osteoporosis for American Woman Aged 45 and Older, 1986," *Bone* 9(4):271-279.

Pickett, F.A. (Jul. 2006). "Bisphosphonate-Associated Osteonecrosis of the Jaw: A Literature Review and Clinical Practice Guidelines," *Journal of Dental Hygiene* 80(3):1-12.

Polverini, P.J. (Aug. 2002). "Angiogenesis in Health and Disease: Insights into Basic Mechanisms and Therapeutic Opportunities," *Journal of Dental Education* 66(8):962-975.

R&D Systems, Inc. (Date Unknown). "Quantikine® Human PDGF-BB Immunoassay," *Package Insert*, Catalog No. DBB00, SBB, and PDB00, located at <http://www.rndsystems.com/pdf/dbb00.pdf>, last visited on Mar. 30, 2010, 16 pages.

Rao, C.D. et al. (Apr. 1986). "Structure and Sequence of the Human C-Sis Platelet-Derived Growth Factor 2 (*SIS/PDGF2*) Transcriptional Unit," *Proc. Natl. Acad. Sci. USA* 83:2392-2396.

Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," *Int. J. Mol. Med.* 23(3):407-413, Abstract Only, 2 pages.

Rasubala, L. et al. "Platelet-derived Growth Factor and Bone Morphogenetic Protein in the Healing of Mandibular Fractures in Rats," *British Journal of Oral and Maxillofacial Surgery*, 2003, 41:173-178.

Robbins, K.C. et al. (Oct. 13, 1983). "Structural and Immunological Similarities Between Simian Sarcoma Virus Gene Product(s) and Human Platelet-Derived Growth Factor," *Nature* 305:605-608.

(56) References Cited

OTHER PUBLICATIONS

Rodeo, S.A. et al. (Dec. 1993). "Tendon Healing in a Bone Tunnel," *J. Bone Joint Surg. Am.* 75-A(12):1795-1803.

Rodeo, S.A. et al. (1999). "Use of Recombinant Human Bone Morphogenic Protein-2 to Enhance Tendon Healing in a Bone Tunnel," *Am. J. Sports Med.* 27(4):476-488.

Rodriguez et al. "Maxillary Sinus Augmentation with Deproteinated Bovine Bone and Platelet Rich Plasma with Simultaneous Insertion of Endosseous Implants," *J. Oral Maxiilofac. Surg.*, 2003, 61:157-163.

Ruggiero, S.L. et al. (2006, e-pub. Jul. 31, 2006). "Bisphosphonate-Related Osteoncerosis of the Jaw: Background and Guidelines for Diagnosis, Staging and Management," *Oral Surgery, Oral Medicine, Oral Pathology, Oral Radiology, and Endodontology* <http://www.sciencedirect.com/science/joumal/10792104> 8 pages.

Russell, T.A. et al. (Date Unknown). "Trigen® IM Nail System Surgical Technique. Trochanteric Antegrade Nail (TAN™)," 24 pages.

Sandberg, "Matrix in Cartilage and Bone Development: Current Views on the Function and Regulation of Major Organic Components," *Annals of Medicine*, 1991, 23:207-217.

Sarment, D.P. et al. (Feb. 1, 2006). "Effect of rhPDGF-BB on Bone Turnover During Periodontal Repair," *Journal of Clinical Periodontolgy* 33(2):135-140.

Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," *Clin. Oral Implants Res.* 14(3):369-372.

Sasai et al. (1994). "Xenopus *chordin*: A Novel Dorsalizing Factor Activated by Organizer-Specific Homeobox Genes," *Cell* 79:779-790.

Saygin et al. "Molecular and Cell Biology of Cementum," *Periodontology*, 2000, 24:73-98.

Schenk, R.K. et al. (Jan./Feb. 1994). "Healing Pattern of Bone Regeneration in Membrane-Protected Defects: A Histologic Study in the Canine Mandible," *Int. J. Oral Maxillofac. Implants* 9(1):13-29.

Schmidt et al. "A review of the effects of insulin-like growth factor and platelet derived growth factor on in vivo cartilage healing and repair," *Osteoarthritis and Cartilage*, 2006, 14(5):403-412.

Schmitt, J.M. et al. (Nov. 1997). "Comparison of Porous Bone Mineral and Biologically Active Glass in Critical-Sized Defects," *J. Periodontol.* 68(11):1043-1053.

Shahgaldi, B.F. et al. (Jan. 1991). "Repair of Cartilage Lesions Using Biological Implants. A Comparative Histological and Biomechanical Study in Goats," *J. Bone Joint Surg. Br.* 73-B(1):57-64.

Sigma (Date Unknown). "Platelet Derived Growth Factor-BB," Product Information Sheet, 2 pages.

Simion, M. et al. (Apr. 1994). "A Comparative Study of the Effectiveness of e-PTFE Membranes With and Without Early Exposure During the Healing Period," *Int. J. Periodontics Restorative Dent.* 14(2):166-180.

Simion, M. et al. (1994). "Vertical Ridge Augmentation Using a Membrane Technique Associated with Osseointegrated Implants," *Int. J. Periodontics Restorative Dent.* 14(6):497-511.

Simion, M. et al. (1995). "Bacterial Penetration in vitro Through GTAM Membrane With and Without Topical Chlorhexidine Application: A Light and Scanning Electron Microscopic Study," *J. Clin. Periodontol.* 22:321-331.

Simion, M. et al. (Feb. 1998). "Vertical Ridge Augmentation Around Dental Implants Using a Membrane Technique and Autogenous Bone or Allografts in Humans," *Int. J. Periodontics Restorative Dent.* 18(1):9-23.

Simion, M. et al. (1999). "Effect of Different Microstructures of e-PTFE Membranes on Bone Regeneration and Soft Tissue Response: A Histologic Study in Canine Mandible," *Clin. Oral Implants Res.* 10:73-84.

Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," *The International Journal of Periodontics & Restorative Dentistry* 26(5):415-423.

Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," *Mayo Clin. Proc.* 81(8):1013-1022.

Smith & Nephew (Date Unknown). "Trigen. Humeral Nail," Surgical Technique Pamphlet, 27 pages.

Solheim, E. "Growth Factors in Bone," *International Orthopedics (SICOT)*, 1998, 22:410-416.

Spindler, K.P. et al. (1995). "Proliferative Response to Platelet-Derived Growth Factor in Young and Old Rat Patellar Tendon," *Connective Tissue Research* 31(2):171-177.

Stephan, E.B. et al. (Apr. 1999). "Anogranic Bovine Bone Supports Osteoblastic Cell Attachment and Proliferation," *J. Periodontol.* 70(4):364-369.

Stephan et al. "Platelet-Derived Growth Factor Enhancement of a Mineral-Collagen Bone Substitute," *J. Periodontal*, Dec. 2000, 71:1887-1892.

Strom, T.B. (Sep. 6, 2005). "Saving Islets from Allograft Rejection," *PNAS USA* 102(36):12651-12652.

Suba et al. "Facilitation of $\beta$-Tricalcium Phosphate-Induced Alveolar Bone Regeneration by Platelet-Rich Plasma in Beage Dogs: A Histologic and Histomorphometric Study," *The International J. of Oral and Maxillofacial Implants*, 2004, 19(6):832-838.

Tadic, D. et al. (2004). "A Novel Method to Produce Hydroxyapatite Objects with Interconnecting Porosity that Avoids Sintering," *Biomaterials* 25(16):3335-3340.

Tamai, N. et al. (2002). "Novel Hydroxyapatite Ceramics with an Interconnective Porous Structure Exhibit Superior Osteoconduction in vivo," *J. Biomed. Mater. Res.* 59:110-117.

Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," *J. Orthop. Res.* 25(17):1358-1368.

Tinti, C. et al. (1996). "Vertical Ridge Augmentation: What is the Limit?" *Int. J. Periodontics Restorative Dent.* 16(3):221-229.

U.S. Appl. No. 10/965,319, filed Oct. 14, 2004, by Lynch.

Van Den Wyngaert, T. et al. (Aug. 2006). "Bisphosphonates and Osteonecrosis of the Jaw: Cause and Effect or a post hoc Fallacy?" *Annals of Oncology* 17(8):1197-1204.

Venkatasatya, M. et al. (2008). *The Effect of PDGF, Vitamin D and PTH on Osteoblasts Derived From Patients on Chronic Bisphosphonate Therapy*, Dissertation for The State University of New York at Buffalo, located at <http://gradworks.umi.com/14/531/1453440.html>, last visited on Mar. 31, 2010, 2 pages. Abstract only.

Virchenko, O. et al. (2008, e-pub. Jul. 4, 2008). "Early Achilles Tendon Healing in Sheep," *Arch. Orthop. Trauma Surg.* 128:1001-1006.

Visnapuu et al. "Distribution of fibroblast growth factors (FGFR-1 and -3) and platelet-derived growth factor receptors (PDGFR) in the rat mandibular condyle during growth," *Orthod. Craniofadal.* 2002, 5:147-153.

Walter, C. et al. (2006, e-pub. Aug. 29, 2006). "Prevalence of Bisphophonate Associated Osteonecrosis of the Jaw within the Filed of Osteonecrosis," *Support Care Center* 6 pages.

Wang, Y. et al. (Feb. 23, 1996). "A Large Family of Putative Transmembrane Receptors Homologous to the Product of the *Drosophila* Tissue Polarity Gene Frizzled," *J. Biol. Chem.* 271(8):4468-4476.

Wang, X.T. et al. (Sep. 2004). "Tendon Healing In Vitro: Genetic Modification of Tenocytes With Exogenous PDGF Gene and Promotion of Collagen Gene Expression," *The Journal of Hand Surgery* 29A(5):884-890.

Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," *J. Bone Joint Surg. Am.* 74-A(1):36-45.

(56) References Cited

OTHER PUBLICATIONS

Wei et al. "Nano-Fibrous Scaffold for Controlled Delivery of Recombinant Human PDGF-BB," *Journal of Controlled Release*, 2006, e-pub. Mar. 3, 2006, 112:103-110.

Wikesjö et al. (1988). "Repair of Periodontal Furcation Defects in Beagle Dogs Following Reconstructive Surgery Including Root Surface Demineralization with Tetracycline Hydrochloride and Topical Fibronectin Application," *J. Clin. Periodontol* 15:73-79.

Wikesjö et al. (1989). "Effects of Subgingival Irrigation on A. actinomycetemcomitans," *J. Clin. Perrodont.* 16:116-119.

Williams et al. "Tissue Engineering: What Does It Mean? Why Is It Important?" *Compendium*, Jan. 2005, 26(1):54-60.

Wisner-Lynch, L.A. (Oct. 2006). "From Passive to Active: Will Recombinant Growth Factor Therapeutics Revolutionize Regeneration?" *Int. J. Periodont. and Rest. Dent.* 26(5):409-411.

Woo, S-B. et al. (May 16, 2006). "Systematic Review: Bisphosphonates and Osteonecrosis of the Jaws," *Annals of Internal Medicine* 144(10):753-761.

Written Opinion of the International Searching Authority mailed on Jun. 18, 2008, for PCT Patent Application No. PCT/US2007/015345, filed on Jul. 2, 2007, 4 pages.

Yang, C. et al. (2003). "Vascular Endothelial Growth Factor Gene Transfection to Enhance the Repair of Avascular Necrosis of the Femoral Head of Rabbit," *Chinese Medical Journal* 116(10):1544-1548.

Yazawa et al. "Basic Studies on the Clinical Applications of Platelet-Rich Plasma," *Cell Transplantation*, 2003, 12:509-518.

Yazawa, M. et al. (May 2004). "Basic Studies on the Bone Formation Ability by Platelet Rich Plasma in Rabbits," *Journal of Craniofacial Surgery* 15(3):439-446.

Yokota, K. et al. (2008, e-pub. Feb. 1, 2008). "Platelet-Rich Plasma Accelerated Surgical Angio-Genesis in Vascular Necrotic Bone. An Experimental Study in Rabbits," *Acta Orhopaedica* 79(1):106-110.

Younger, E.M. et al. (1989). "Morbidity at Bone Graft Donor Sites," *J. Orthop. Trauma* 3(3):192-195.

Zavras, A.I. et al. (2006). "Bisphosphonates Are Associated With Increased Risk for Jaw Surgery in Medical Claims Data: Is it Osteonecrosis?" *J. Oral Maxillofac. Surg.* 64:917-923.

Zhu et al. "Gene Transfer and Expression of Platelet-Derived Growth Factors Modulate Periodontal Cellular Activity," *J. Dent Res*, 2001, 80(3):892-897.

Anonymous (2003). "The European Market for Dental Bone Graft Substitutes," *Implant Dentistry* 12(1):3-5.

Antoniades, H.N. et al. (1991). "Molecular Mechanism of Tissue Repair: Injury Induces Expression of PDGF-B and its Receptor," Abstract No. 2156, *J. Dental Res.* 70:536.

Buser, D. et al. (1991). "Effects of Growth Factors on Bone Regeneration Around Titanium Implants," Abstract No. 282, *J. Dental Res.* 70:301.

Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," *J. Periodontol.* 71(1):1743-1749.

Daniels, T.R. et al. (2008). "Application of rhPDGF-BB in Foot and Ankle Fusion Procedures," Chapter 19 in *Tissue Engineering: Applications in Maxillofacial Surgery and Periodontics*, Second Edition, Lynch, S.E. et al. eds., Quintessence Publishing Co.: Hanover Park, IL, pp. 267-275.

Finkelman, R.D. et al. (1995). "Systematic PDGF ± Alendronate Increases Bone Density in OVX Rats," Abstract No. 1281, *J. Dental Res.* 74:172.

Giannobile, W.V. et al. (1994). "Synergistic Effects of Insulin-Like Growth Factors-I (IGF-I) with Other Growth Factors on Bone Formation in vitro," Abstract No. 831, *J. Dental Res.* 73:205.

Giannobile, W.V. et al. (1994). "Platelet Derived Growth Factor (PDGF) and Insulin-Like Growth Factor (IGF-I) Enhances Periodontal Regeneration in Macaca Fascicularis," Abstract No. 28, *Tissue Repair* 9(3 Suppl.):29.

Giannobile, W.V. (2008). "Advances in Gene Therapy for Periodontal Bioengineering," Chapter 3 in *Tissue Engineering: Applications in Maxillofacial Surgery and Periodontics*, Second Edition, Lynch, S.E. et al. eds., Quintessence Publishing Co.: Hanover Park, IL, pp. 37-46.

Hollinger, J.O. et al. (Feb. 2008). "Recombinant Human Platelet Derived Growth Factor: Biology and Clinical Applications," *J. Bone & Joint Surgery* 90-A(Suppl. 1):48-54.

Hollinger, J.O. et al. (2008). "Protein Therapeutics and Bone Healing," Chapter 1 in *Tissue Engineering: Applications in Maxillofacial Surgery and Periodontics*, Second Edition, Lynch, S.E. et al. eds., Quintessence Publishing Co.: Hanover Park, IL, pp. 3-25.

Jensen, O.T. et al. (2008). "Alveolar Distraction Osteogenesis and Tissue Engineering," Chapter 14 in *Tissue Engineering: Applications in Maxillofacial Surgery and Periodontics*, Second Edition, Lynch, S.E. et al. eds., Quintessence Publishing Co.: Hanover Park, IL, pp. 203-219.

Jensen, O.T. (2008). "Dentoalveolar Modification with an Osteoperiosteal Flap and rhPDGF-BB," Chapter 15 in *Tissue Engineering: Applications in Maxillofacial Surgery and Periodontics*, Second Edition, Lynch, S.E. et al. eds., Quintessence Publishing Co.: Hanover Park, IL, pp. 220-225.

Li, J. et al. (1994). "Systematic Administration of PDGF With or Without Alendronate Increases Spine and Whole Body Bone Mineral Density in OVX Rats," Abstract No. 59, *Sixteenth Annual Meeting of the American Society for Bone and Mineral Research*, Kansas City, MO. , Sep. 9-13, 1994, p. S135.

Lynch, S.E. et al. (1988). "Synergistic Effects of Recombinant Platelet-Derived Growth Factor Two and Insulin-Like Growth Factor-I in Wound Healing," Abstract No. 585, *J. Dental Res.* 67:186.

Lynch, S.E. et al. (1988). "Potential Role of Platelet-Derived and Insulin-Like Growth Factors in Periodontal Regeneration," Abstract No. 586, *J. Dental Res.* 67:186.

Lynch, S.E. et al. (Dec. 1988). "Growth Factors in Wound Healing: Single and Synergistic Effects," Abstract No. 238, *J. Cell Biol.* 107(6 Part 3):46a.

Lynch, S.E. et al. (1989). "Comparative Effects of Growth Factors on Soft Tissue Repair," Abstract No. 1153, *J. Dental Res.* 68:326.

Lynch, S.E. et al. (1992). "Effect of PDGF-B and IGF-I on Bone Regeneration," Abstract No. 82, *J. Dental Res.* 71:116.

Lynch, S.E. (1993). "Comparison of Results in the Canine and Primate Models Using a Single Regenerative Therapy," Abstract No. 37, *J. Dental Res.* 72:108.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," *Wound Repair and Regeneration Abstract*, 2(1):84.

Lynch, S.E. et al. (1994). "Polypeptide Growth Factors: Molecular Mediators of Tissue Repair," Chapter 33 in *Molecular Pathogenesis of Periodontal Disease*, Genco, R. et al eds., A.S.M. Press: Washington DC, pp. 415-425.

Lynch, S.E. (1994). "The Role of Growth Factors in Periodontal Repair and Regeneration," Chapter 11 in *Periodontal Regeneration: Current Status and Directions*, Polson, A. ed. Quintessence Publishing Co, Inc: Chicago, IL, 11:179-197.

Lynch, S.E. et al. (2008). "Use of rhPDGF to Improve Bone and Periodontal Regeneration," Chapter 6 in *Tissue Engineering: Applications in Maxillofacial Surgery and Periodontics*, Second Edition, Lynch, S.E. et al. eds., Quintessence Publishing Co.: Hanover Park, IL, pp. 87-102.

Marx, R.E. (2008). "Application of Tissue Engineering Principles to Clinical Practice," Chapter 4 in *Tissue Engineering: Applications in Maxillofacial Surgery and Periodontics*, Second Edition, Lynch, S.E. et al. eds., Quintessence Publishing Co.: Hanover Park, IL, pp. 47-63.

Marx, R.E. (2008). "Use of PRP in Oral and Maxillofacial Surgery and Periodontology," Chapter 9 in *Tissue Engineering: Applications in Maxillofacial Surgery and Periodontics*, Second Edition, Lynch, S.E. et al. eds., Quintessence Publishing Co.: Hanover Park, IL, pp. 132-144.

McAllister, B. et al. (1998). "Long-term Evaluation of Sinus Grafting with Bio-Oss® in the Chimpanzee," Abstract No. 1097, *J. Dental Res.* 77:769.

McGuire, M.K. (2008). "Soft Tissue Engineering Applications in Dentistry," Chapter 7 in *Tissue Engineering: Applications in Maxil-*

(56) References Cited

OTHER PUBLICATIONS

*lofacial Surgery and Periodontics*, Second Edition, Lynch, S.E. et al. eds., Quintessence Publishing Co.: Hanover Park, IL, pp. 103-118.
Nevins, M.L. et al. (2005). "Three-Dimensional Micro-Computed Tomographic Evaluation of Periodontal Regeneration: A Human Report of Intrabony Defects Treated with Bio-Oss Collagen," *Int. J. Periodontics Restorative Dent.* 25(4)365-373.
Nevins, M. et al. (2008). "Treatment of Advanced Periodontal Defects Using Bioactive Therapies," Chapter 5 in *Tissue Engineering: Applications in Maxillofacial Surgery and Periodontics*, Second Edition, Lynch, S.E. et al. eds., Quintessence Publishing Co.: Hanover Park, IL, pp. 67-86.
Nevins, M.L. et al. (2008). "Site Development for Implant Placement: Regenerative and Esthetic Techniques in Oral Plastic Surgery," Chapter 8 in *Tissue Engineering: Applications in Maxillofacial Surgery and Periodontics*, Second Edition, Lynch, S.E. et al. eds., Quintessence Publishing Co.: Hanover Park, IL, pp. 119-131.
Nickols, J.C. et al. (2008). "The Role of Growth Factors in Tendon Healing," Chapter 20 in *Tissue Engineering: Applications in Maxillofacial Surgery and Periodontics*, Second Edition, Lynch, S.E. et al. eds., Quintessence Publishing Co.: Hanover Park, IL, pp. 276-289.
Ruiz, G. et al. (1991). "Short Term Administration of Growth Factors Enhances Periodontal Regeneration," Abstract No. 1615, *J. Dental Res.* 70:468.
Schmidt, M.B. et al. (2008). "Tissue Engineering Strategies in the Treatment of TMDs," Chapter 18 in *Tissue Engineering: Applications in Maxillofacial Surgery and Periodontics*, Second Edition, Lynch, S.E. et al. eds., Quintessence Publishing Co.: Hanover Park, IL, pp. 252-264.
Simion, M. et al. (2008). "Minimally Invasive Strategies for Vertical Ridge Augmentation," Chapter 10 in *Tissue Engineering: Applications in Maxillofacial Surgery and Periodontics*, Second Edition, Lynch, S.E. et al. eds., Quintessence Publishing Co.: Hanover Park, IL, pp. 145-158.
Spector, M. (2008). "Basic Principles of Scaffolds in Tissue Engineering," Chapter 2 in *Tissue Engineering: Applications in Maxillofacial Surgery and Periodontics*, Second Edition, Lynch, S.E. et al. eds., Quintessence Publishing Co.: Hanover Park, IL, pp. 26-36.
Teraoka, K. et al. (2004). "Construction of an Interconnected Pore Network Using Hydroxyapatite Beads," *Key. Eng. Mater.* 254-256:257-259.
Teraoka, K. et al. (Sep. 2004). "Construction of Interconnected Pore Network Using Hydroxyapatite Small Components," *Trans. Mater. Res. Soc. Jpn.* 29(6):2919-2921.
Wang, L. et al. (2004). "Three-Dimensional Porous Network Structure Developed in Hydroxyapatite-Based Nanocomposites Containing Enzyme Pretreated Silk Fibronin," *J. Nanopart.* 6(1):91-98.
Wiesen, R.J. et al. (1998). "Efficacy of Bovine Bone Mineral in Vertical Osseous Defects," Abstract No. 1165, *J. Dental Res.* 77:777.
BioMimetic Therapeutics (Aug. 21, 2002). "Orthovita and BioMimetic Enter into a Supply Agreement," located at <http://biomimetics.com/cgi-bin/aw/acuweb.cgi?s=biomimetics&t=pressreleasedtl.htm&StoryID=82&>, last visited on May 18, 2010, 6 pages.
BioMimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressreleasedtl.htm&StoryID=76&>, last visited on May 18, 2010, 5 pages.
BioMimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressreleasedtl.htm&StoryID=83&>, last visited on May 18, 2010, 6 pages.
BioMimetic Therapeutics (Jul. 15, 2004). "BioMimetic Pharmaceuticals' Receives Approvable Recommendation from FDA Advisory Panel for GEM 21S®," located at <http://biomimetics.com/cgi-bin/aw/acuweb.cgi?s=biomimetics&t=pressreleasedtl.htm&StoryID=78&>, last visited on May 18, 2010, 6 pages.
BioMimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics&t=pressreleasedtl.htm&StoryID=79&>, last visited on May 20, 2010, 5 pages.
BioMimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics&t=pressreleasedtl.htm&StoryID=80&>, last visited on May 18, 2010, 6 pages.
BioMimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressreleasedtl.htm&StoryID=81&>, last visited on May 20, 2010, 6 pages.
BioMimetic Therapeutics (Nov. 21, 2005). "BioMimetic Therapeutics Announces FDA Approval of GEM 21S® Growth-Factor Enhanced Matrix for the Treatment of Periodontally-Related Bone Defects," located at <http://biomimetics.com/cgi-bin/aw/acuweb.cgi?s=biomimetics&t=pressreleasedtl.htm&StoryID=87&>, last visited on May 18, 2010, 6 pages.
BioMimetic Therapeutics (Mar. 20, 2006). "BioMimetic Therapeutics Initiates Trials with Novel Bio-Active Drug-Device Combination Bone Graft in Two Orthopedic Indications," located at <http://biomimetics.com/cgi-bin/aw/acuweb.cgi?s=biomimetics&t=pressreleasedtl.htm&StoryID=118&>, last visited on May 18, 2010, 6 pages.
BioMimetic Therapeutics (Jul. 11, 2006). "BioMimetic Therapeutics Successfully Completes Enrollment in Three Orthopedic Pilot Clinical Trials for GEM OS1™ Bone Graft; Canadian Study Expanded to 60 Patients," located at <http://biomimetics.com/cgi-bin/aw/acuweb.cgi?s=biomimetics&t=pressreleasedtl.htm&StoryID=93&>, last visited on May 18, 2010, 6 pages.
BioMimetic Therapeutics (Sep. 14, 2006). "BioMimetic Therapeutics Clinical Investigators to Receive Award from American Academy of Periodontolgy for Outstanding Publication; Clinical Investigators to Present Data at Annual AAP Meeting," located at <http://biomimetics.com/cgi-bin/aw/acuweb.cgi?s=biomimetics&t=pressreleasedtl.htm&StoryID=94&>, last visited on May 18, 2010, 6 pages.
BioMimetic Therapeutics (Sep. 27, 2006). "BioMimetic Therapeutics Adds Key Talent to Board of Directors," located at <http://biomimetics.com/cgi-bin/aw/acuweb.cgi?s=biomimetics&t=pressreleasedtl.htm&StoryID=97&>, last visited on May 20, 2010, 6 pages.
BioMimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressreleasedtl.htm&StoryID=101&>, last visited on May 18, 2010, 7 pages.
BioMimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressreleasedtl.htm&StoryID=104&>, last visited on May 18, 2010, 7 pages.
BioMimetic Therapeutics (Jan. 25, 2007). "BioMimetic Therapeutics Reports Positive Clinical Results Using GEM OS® 1 to Treat Distal Radius Fractures," located at <http://biomimetics.com/cgi-bin/aw/acuweb.cgi?s=biomimetics&t=pressreleasedtl.htm&StoryID=105&>, last visited on May 18, 2010, 6 pages.
BioMimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at <http://biomimetics.com/cgi-bin/aw/acuweb.cgi?s=biomimetics&t=pressreleasedtl.htm&StoryID=113&>, last visited on May 18, 2010, 8 pages.
Biomimetic Therapeutics (May 10, 2007). "BioMimetic Therapeutics to Report 2007 First Quarter Financial Results on May 14," located at <http://biomimetics.com/cgi-bin/aw/acuweb.

(56) References Cited

OTHER PUBLICATIONS cgi?s=biomimetics&t=pressreleasedtl.htm&StoryID=111&>, last visited on May 18, 2010, 4 pages.
BioMimetic Therapeutics (May 14, 2007). "BioMimetic Therapeutics Reports 2007 First Quarter Results; Company Added to NASDAQ Biotechnology Index," located at <http://biomimetics.com/cgi-bin/aw/acuweb.cgi?s=biomimetics&t=pressreleasedtl.htm&StoryID=116&>, last visited on May 18, 2010, 7 pages.
BioMimetic Therapeutics (Jun. 7, 2007). "BioMimetic Therapeutics Initiates Enrollment in E.U. Registration Trial for GEM OS® 1 Bone Graft; U.S. GEM OS1 Pivotal Study Protocol Amended to Allow Shorter Follow-Up Time and More Patients," located at <http://biomimetics.com/cgi-bin/aw/acuweb.cgi?s=biomimetics&t=pressreleasedtl.htm&StoryID=119&>, last visited on May 18, 2010, 6 pages.
BioMimetic Therapeutics (Jul. 13, 2007). "BioMimetic Therapeutics' Clinical Investigator Presents Positive Interim Data on U.S. and Canadian Foot and Ankle Clinical Trials," located at <http://biomimetics.com/cgi-bin/aw/acuweb.cgi?s=biomimetics&t=pressreleasedtl.htm&StoryID=123&>, last visited on May 18, 2010, 8 pages.
BioMimetic Therapeutics (Aug. 14, 2007). "BioMimetic Therapeutics Reports 2007 Second Quarter Results," located at <http://biomimetics.com/cgi-bin/aw/acuweb.cgi?s=biomimetics&t=pressreleasedtl.htm&StoryID=125&>, last visited on May 18, 2010, 7 pages.
BioMimetic Therapeutics (Nov. 13, 2007). "BioMimetic Therapeutics Reports 2007 Third Quarter Results," located at <http://biomimetics.com/cgi-bin/aw/acuweb.cgi?s=biomimetics&t=pressreleasedtl.htm&StoryID=127&>, last visited on May 18, 2010, 7 pages.
BioMimetic Therapeutics (Dec. 13, 2007). "BioMimetic Therapeutics reports Positive Clinical Results for GEM OS® 1 in Canadian Foot and Ankle Fusion Study; Clinical Success Rate of 90% Achieved in High Risk Patient Population," located at <http://biomimetics.com/cgi-bin/aw/acuweb.cgi?s=biomimetics&t=pressreleasedtl.htm&StoryID=131&>, last visited on May 18, 2010, 6 pages.
BioMimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at <http://biomimetics.com/cgi-bin/aw/acuweb.cgi?s=biomimetics&t=pressreleasedtl.htm&StoryID=149&>, last visited on May 18, 2010, 7 pages.
BioMimetic Therapeutics (Feb. 29, 2008). "BioMimetic Therapeutics, Inc. to Highlight Clinical and Preclinical Activities at ORS and AAOS Meetings," located at <http://biomimetics.com/cgi-bin/aw/acuweb.cgi?s=biomimetics&t=pressreleasedtl.htm&StoryID=136&>, last visited on May 18, 2010, 6 pages.
BioMimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at <http://biomimetics.com/cgi-bin/aw/acuweb.cgi?s=biomimetics&t=pressreleasedtl.htm&StoryID=138&>, last visited on May 18, 2010, 6 pages.
BioMimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at <http://biomimetics.com/cgi-bin/aw/acuweb.cgi?s=biomimetics&t=pressreleasedtl.htm&StoryID=137&>, last visited on May 18, 2010, 8 pages.
BioMimetic Therapeutics (Aug. 11, 2008). "BioMimetic Therapeutics Reports 2008 Second Quarter Results; Positive Results Achieved with Augment™ Injectable Bone Graft to Enhance Healing in Foot and Ankle Fusions," located at <http://biomimetics.com/cgi-bin/aw/acuweb.cgi?s=biomimetics&t=pressreleasedtl.htm&StoryID=151&>, last visited on May 18, 2010, 8 pages.
BioMimetic Therapeutics (Sep. 23, 2008). "BioMimetic Therapeutics Announces No Changes Requested by Independent Data Monitoring Committee to Pivotal Trial Design for Augment™ Bone Graft; 268 of 396 Patients Enrolled to Date in U.S. Pivotal Trial," located at <http://biomimetics.com/cgi-bin/aw/acuweb.cgi?s=biomimetics&t=pressreleasedtl.htm&StoryID=153&>, last visited on May 18, 2010, 7 pages.
BioMimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396 Patients Enrolled," located at <http://biomimetics.com/cgi-bin/aw/acuweb.cgi?s=biomimetics&t=pressreleasedtl.htm&StoryID=159&>, last visited on May 18, 2010, 6 pages.
BioMimetic Therapeutics (Nov. 10, 2008). "BioMimetic Therapeutics Reports 2008 Third Quarter Results," located at <http://biomimetics.com/cgi-bin/aw/acuweb.cgi?s=biomimetics&t=pressreleasedtl.htm&StoryID=157&>, last visited on May 18, 2010, 8 pages.
BioMimetic Therapeutics (Nov. 21, 2008). "BioMimetic Therapeutics, Inc. Announces Patent Allowance from the United Stats Patent and Trademark Office for PDGF Compositions Patent; Expanded Protection for Augment™, Augment™ Injectable and GEM 21S® Until 2024," located at <http://biomimetics.com/cgi-bin/aw/acuweb.cgi?s=biomimetics&t=pressreleasedtl.htm&StoryID=163&>, last visited on May 18, 2010, 5 pages.
BioMimetic Therapeutics (Dec. 11, 2008). "BioMimetic Therapeutics, Inc. Achieves Patient Enrollment Target (396) in North American Pivotal Study for Augment™ Bone Graft," located at <http://biomimetics.com/cgi-bin/aw/acuweb.cgi?s=biomimetics&t=pressreleasedtl.htm&StoryID=169&>, last visited on May 18, 2010, 5 pages.
BioMimetic Therapeutics (Jan. 7, 2009). "BioMimetic Therapeutics, Inc. Closes Enrollment with 436 Patients in North American Pivotal Study for Augment™ Bone Graft; Company Will File Modular PMA with the FDA Beginning This Spring," located at <http://biomimetics.com/cgi-bin/aw/acuweb.cgi?s=biomimetics&t=pressreleasedtl.htm&StoryID=168&>, last visited on May 18, 2010, 5 pages.
BioMimetic Therapeutics (Feb. 19, 2009). "BioMimetic Therapeutics, Inc. To Highlight Pre-Clinical and Clinical Activities at ORS and AAOS Meetings; Company to Host an Analyst and Investor Meeting Feb. 26," located at <http://biomimetics.com/cgi-bin/aw/acuweb.cgi?s=biomimetics&t=pressreleasedtl.htm&StoryID=154&>, last visited on May 18, 2010, 6 pages.
BioMimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressreleasedtl.htm&StoryID=160&>, last visited on May 18, 2010, 11 pages.
BioMimetic Therapeutics (May 7, 2009). "BioMimetic Therapeutics Releases 2009 First Quarter Financial Results," located at <http://biomimetics.com/cgi-bin/aw/acuweb.cgi?s=biomimetics&t=pressreleasedtl.htm&StoryID=167&>, last visited on May 18, 2010, 8 pages.
BioMimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressreleasedtl.htm&StoryID=185&>, last visited on May 18, 2010, 8 pages.
BioMimetic Therapeutics (Oct. 13, 2009). "BioMimetic Announces Positive Top-Line Data from its Augment Bone Graft North American Pivotal Trial; Augment Demonstrates Non-Inferiority to Autograft," located at <http://biomimetics.com/cgi-bin/aw/acuweb.cgi?s=biomimetics&t=pressreleasedtl.htm&StoryID=188&>, last visited on May 18, 2010, 8 pages.
BioMimetic Therapeutics (Nov. 3, 2009). "BioMimetic Therapeutics Receives First Orthopedic Marketing Approval for Augment Bone Graft," located at <http://biomimetics.com/cgi-bin/aw/acuweb.cgi?s=biomimetics&t=pressreleasedtl.htm&StoryID=190&>, last visited on May 18, 2010, 6 pages.
BioMimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at <http://biomimetics.com/

(56) References Cited

OTHER PUBLICATIONS cgi-bin/aw/acuweb.cgi?s=biomimetics&t=pressreleasedtl.htm& StoryID=191&>, last visited on May 18, 2010, 8 pages.
BioMimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressreleasedtl.htm&StoryID=199&>, last visited on May 18, 2010, 5 pages.
BioMimetic Therapeutics (Mar. 4, 2010). "BioMimetic Therapeutics, Inc. to Highlight Pre-Clinical and Clinical Activities at ORS and AAOS Meetings; Company to Host Analyst and Investor Meeting on Mar. 11," located at <http://biomimetics.com/cgi-bin/aw/acuweb.cgi?s=biomimetics&t=pressreleasedtl.htm&StoryID=201&>, last visited on May 18, 2010, 6 pages.
BioMimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s=biomimetics&t=pressreleasedtl.htm&StoryID=202&>, last visited on May 18, 2010, 6 pages.
BioMimetic Therapeutics (Mar. 11, 2010). "BioMimetic Therapeutics Reports 2009 Fourth Quarter and Year End Earnings Results; Company Releases Additional Pivotal Data on Augment," located at <http://biomimetics.com/cgi-bin/aw/acuweb.cgi?s=biomimetics&t=pressreleasedtl.htm&StoryID=203&>, last visited on May 18, 2010, 11 pages.
BioMimetic Therapeutics (Mar. 12, 2010). "Morningstar® Document Research<sup>SM</sup> Form 10-K," United States Securities and Exchange Commission Annual Report, located at <http://investor.biomimetics.com/phoenix.zhtml?c=196896&p=irol-sec>, last visited on May 19, 2010, 247 pages.
Lee, Y-M. et al. (Mar. 2000). "The Bone Regenerative Effect of Platelet-Derived Growth Factor-BB Delivered With a Chitosan/Tricalcium Phosphate Sponge Carrier," *J. Periodontal.* 71(3):418-424.
Coleman, S.H. et al. (Dec. 2003). "Chronic Rotator Cuff Injury and Repair Model in Sheep," *The Journal of Bone and Joint Surgery* 85-A(12):2391-2402.
International Search Report mailed on Jun. 18, 2008, for PCT Patent Application No. PCT/US2007/015345, filed on Jul. 2, 2007, 3 pages.
Mheta, V. et al. (Apr.-Jun. 2005). "The Use of Growth Factors on Tendon Injuries," *Journal of Hand Therapy* 18:87-92.
Nevins M. et al. (Dec. 2005). "Platelet-Derived Growth Factor Stimulates Bone Fill and Rate of Attachment Level Gain: Results of a Large Multicenter Randomized Controlled Trial," *Journal of Periodontology* 76:2205-2215.
Woo, S.L-Y. et al. (1998). "Engineering the Healing of the Rabbit Medical Collateral Ligament," *Medical and Biological Engineering and Computing* 36:359-364.
Zimmer, Inc. (2005). "Zimmer® Collagen Repair Patch," Product No. 04-4100-001-00, 6 pages.
Creaney, L. et al. (May 2008, e-pub. Nov. 5, 2007). "Growth Factor Delivery Methods in the Management of Sports Injuries: The State of Play," *Br. J. Sports Med.* 42(5):314-320, Abstract Only.
Donnelly, B.P. et al. (Jul. 2006). "Nucleotide Structure of Equine Platelet-Derived Growth Factor-A and -B and Expression in Horses with Induced Acute Tendinitis," *Am. J. Vet. Res.* 67(7):1218-1225, Abstract Only.
Franco, B. et al. (Jan.-Jun. 2008). "Tissue Engineering Approaches for the Construction of a Completely Autologous Tendon Substitute," *Indian J. Plast. Surg.* 41(1):38-46, 13 pages.
Gelberman, R.H. et al. (Mar. 2007). "The Early Effects of Sustained Platelet-Derived Growth Factor Administration on the Functional and Structural Properties of Repaired Intrasynovial Flexor Tendons: An in vivo Biomechanic Study at 3 Weeks in Canines," *J. Hand Surg. Am.* 32(3):373-379, Abstract Only.
Hoffmann, A. et al. (Dec. 2007, e-pub. Jul. 19, 2007). "Tendon and Ligament Engineering in the Adult Organism: Mesenchymal Stem Cells and Gene-Therapeutic Approaches," *Int. Orthop.* 31(6):791-797.

International Search Report mailed on Oct. 11, 2010, for PCT Patent Application No. PCT/US2009/056418, filed on Sep. 9, 2009, 2 pages.
Liang, H.W. et al. (Aug. 2009). "Effect of Platelet-Derived Growth Factor-BB on Proliferation of Tendon Cells Cultured in vitro," *Zhonghua Shao Shang Za Zhi* 25(4):298-300, Abstract Only.
Lynch, S.E. (1991). "Platelet-Derived Growth Factor and Insulin-Like Growth Factor. I: Mediators of Healing Soft Tissue and Bone Wounds," *Periodontol Case Reports NE Soc. Periodontists Bull.* 13(2):13-20.
McCarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," *J. Orthop. Res.* 27(8):1033-1042, Abstract Only.
Pietrzak, W.S. et al. (Jul. 2000). "Calcium Sulfate Bone Void Filler: A Review and a Look Ahead," *J. Craniofac. Surg.* 11(4):327-333; discussion p. 334.
Qiu, Y. et al. (2009). "Combination of PDGF-BB and bFGF Reduces Differentiation but Maintains Proliferation of Human Tenocytes in Low Bovine Serum Culture in vitro," *European Cells and Materials* 18(Suppl. 2):86.
Qu, Z. et al. (Nov. 1994). "Immunolocalization of Basic Fibroblast Growth Factor and Platelet-Derived Growth Factor-A During Adjuvant Arthritis in the Lewis Rat," *Am. J. Pathol.* 145(5):1127-1139.
Riley, G. (2004, e-pub. Jul. 16, 2003). "The Pathogenesis of Tendinopathy. A Molecular Perspective," *Rheumatology* 43(2):131-142.
Rolf, C.G. et al. (2001). "Increased Cell Proliferation and Associated Expression of PDGFRβ Causing Hypercellularity in Patellar Tendinosis," *Rheumatology* 40:256-261.
Sakiyama-Elbert, S.E. et al. (Nov. 2008). "Controlled-Release Kinetics and Biologic Activity of Platelet-Derived Growth Factor-BB for Use in Flexor Tendon Repair," *J. Hand Surg. Am.* 33(9):1548-1557, Abstract Only.
Schmidt, C.C. et al. (Mar. 1995). "Effect of Growth Factors on the Proliferation of Fibroblasts from the Medial Collateral and Anterior Cruciate Ligaments," *J. Orthop. Res.* 13(2):184-190, Abstract Only.
Schnabel, L.V. et al. (Feb. 2007). "Platelet Rich Plasma (PRP) Enhances Anabolic Gene Expression Patterns in Flexor Digitorum Superficialis Tendons," *J. Orthop. Res.* 25(2):230-240, Abstract Only.
Sharma, P. et al. (2008). "Tendinopathy and Tendon Injury: The Future," *Disability and Rehabilitation* 30(20-22):1733-1745.
Thompoulos, S. et al. (May 2005). "Effect of Several Growth Factors on Canine Flexor Tendon Fibroblast Proliferation and Collagen Synthesis in vitro," *J. Hand Surg. Am.* 30(3):441-447, Abstract Only.
Thomopoulos, S. et al. (Sep. 2009, e-pub. Mar. 25, 2009). "Enhanced Flexor Tendon Healing through Controlled Delivery of PDGF-BB," *J. Orthop. Res.* 27(9):1209-1215, Abstract Only.
Thomopoulos, S. et al. (Feb. 2010, e-pub. Nov. 24, 2009). "bFGF and PDGF-BB for Tendon Repair: Controlled Release and Biologic Activity by Tendon Fibroblasts In Vitro," *Ann. Biomed. Eng.* 38(2):225-234.
Wong, M.W. et al. (Oct. 2003). "Effect of Dexamethasone on Cultured Human Tenocytes and its Reversibility by Platelet-Derived Growth Factor," *Journal of Bone and Joint Surgery American* 85-A(10)1914-1920, Abstract Only.
Written Opinion of the International Searching Authority mailed on Oct. 11, 2010, for PCT Patent Application No. PCT/US2009/056418, filed on Sep. 9, 2009, 8 pages.
Chan, B.P. et al. (Jul. 2006). "Supplementation-time Dependence of Growth Factors in Promoting Tendon Healing," *Clinical Orthopaedics and Related Research* 448:240-247.
Gelberman, R.H. et al. (Mar. 2007). "The Early Effects of Sustained Platelet-Derived Growth Factor Administration on the Functional and Structural Properties of Repaired Intrasynovial Flexor Tendons: An in vivo Biomechanic Study at 3 Weeks in Canines," *J. Hand Surg. Am.* 32A(3):373-379.
Non-Final Office Action mailed on Oct. 21, 2010, for U.S. Appl. No. 11/778,498, filed Jul. 16, 2007, 18 pages.

(56) References Cited

OTHER PUBLICATIONS

Premdas, J. et al. (2001). "The Presence of Smooth Muscle Action in Fibroblasts in the Torn Human Rotator Cuff," *Journal of Orthopaedic Research* 19:221-238.

Shigenobu, T., "Effects of Platelet Derived Growth Factor on Lacerated Tendons," Journal of Hiroshima University School of Medicine, Feb. 2000, vol. 48, No. 1, pp. 1-16 (English translation).

* cited by examiner

Prior Art Technique

PDGF Pad incorporated into sutures

PDGF pouch sutured over repaired tear

COMPOSITIONS AND METHODS FOR TREATING ROTATOR CUFF INJURIES

RELATED APPLICATION DATA

The present application claims priority under 35 U.S.C. §119(e) to U.S. Provisional Patent Application Ser. No. 60/817,874 filed Jun. 30, 2006.

FIELD OF THE INVENTION

The present invention relates to compositions and methods useful for attaching tendon to bone, particularly for repairing rotator cuff injury.

BACKGROUND OF THE INVENTION

Hundreds of thousands of people experience tendon ruptures and tendon detachments from bone annually. Rotator cuff tears are among the most common injuries observed by practitioners of sports medicine. Approximately 400,000 rotator cuff repair surgeries are performed in the United States annually.

The rotator cuff is a group of four tendons which converge and surround the front, back, and top of the head of the humerus shoulder joint. These tendons are connected individually to short muscles that originate from the scapula. The muscles are referred to as the "SITS" muscles-supraspinatus, infraspinatus, teres minor and subscapularis. The muscles function to provide rotation and elevate the arm and give stability to the shoulder joint. When the muscles contract, they pull on the rotator cuff tendons, causing the shoulder to rotate upward, inward, or outward. There is a bursal sac between the rotator cuff and acromion that allows the muscles to glide freely when moving.

Rotator cuff tendons are susceptible to tears, which are a common source of shoulder pain. The tendons generally tear off at their insertion (attachment) onto the humeral head. Injuries to the rotator cuff may be present as complete evulsions, or L- or U-type partial tears. Pain, loss of motion and weakness may occur when one of the rotator cuff tendons tears. When rotator cuff tendons are injured or damaged, the bursa often becomes inflamed and may be an additional source of pain.

Notwithstanding surgical instrumentation and advanced techniques, the incidence of re-injury following repair of the rotator cuff is high, with some estimates approaching 70%. The failure of rotator cuff repairs has been attributed to the poor healing and reattachment of the muscles that insert on the humeral head. The normal fibrotic and proliferative response among tendon fibroblasts and mesenchymal stem cells is diminished within the shoulder. This inadequate healing response therefore transfers the burden of tendon reattachment and integrity to the mechanical strength of the sutures. Over time, the sutures break down and tear away from bone and/or tendon, causing re-injury of the shoulder. The problem has been documented in numerous studies employing the use of animal models. Coleman and colleagues report in *The Journal of Bone and Joint Surgery* 85:2391-2402 (2003) that the repaired infraspinatus muscle of the shoulder is capable of producing only 63% of the normal contraction force normal at 12 weeks after repair using a sheep model of chronic injury.

In view of the problems associated with rotator cuff repairs, it would be desirable to provide compositions and methods operable to improve the healing response associated with rotator cuff repairs. In particular, it would be desirable to provide compositions and methods which enhance fibrotic and proliferative responses among tendon fibroblasts and mesenchymal stems cells thereby promoting healing of a torn rotator cuff and tendon reattachment to the humeral head.

SUMMARY

The present invention provides compositions and methods for the treatment and/or repair of damaged tendons. In some embodiments, compositions and methods of the present invention are useful in the attachment or reattachment of tendons to bone, and may be applied to any tendon reattachment. In some embodiments, compositions and methods of the present invention enhance tendon attachment to bone by strengthening the tendon and/or bone at the site of tendon attachment to the bone. Moreover, the treatment of tendons encompasses application of compositions of the present invention to tendons, including damaged or injured tendons, such as tendons exhibiting tearing, delamination, and/or any other strain or deformation. Tendons which may be reattached to bone and/or treated by compositions and methods of the present invention include, but are not limited to, tendons of the subscapularis, supraspinatus, infraspinatus, teres minor, rectus femoris, tibialis posterior, and quadraceps femoris, as well as the Achilles Tendon, patellar tendon, abductor and adductor tendons, or other tendons of the hip.

In accordance with some embodiments of the present invention, there are provided compositions and methods for the treatment of rotator cuff tears. The present compositions and methods facilitate the healing response to rotator cuff repairs and tendon reattachment to the humeral head.

In one aspect, a composition provided by the present invention for promoting tendon reattachment to the humeral head comprises a solution comprising platelet derived growth factor (PDGF) and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. The concentration of PDGF within the solution may be within any of the concentration ranges stated above.

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF such as recombinant human PDGF-BB (rhPDGF-BB).

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with a preferred embodiment, the rhPDGF-BB comprises at least 65% of intact rhPDGF-B (1-109).

A biocompatible matrix, according to some embodiments of the present invention, comprises a bone scaffolding material. In some embodiments, a bone scaffolding material comprises calcium phosphate. Calcium phosphate, in one embodiment, comprises β-tricalcium phosphate (β-TCP)

In another aspect, the present invention provides a composition comprising a PDGF solution disposed in a biocompatible matrix, wherein the biocompatible matrix comprises a bone scaffolding material and a biocompatible binder. The PDGF solution may have a concentration of PDGF as described above. A bone scaffolding material, in some embodiments, comprises calcium phosphate. In one embodiment, a calcium phosphate comprises a β-TCP. In one aspect, biocompatible matrices may include calcium phosphate particles with or without biocompatible binders or bone allograft such as demineralized freeze dried bone allograft (DFDBA) or particulate demineralized bone matrix (DBM). In another aspect, biocompatible matrices may include bone allograft such as DFDBA or DBM.

Moreover, a biocompatible binder, according to some embodiments of the present invention, comprises proteins, polysaccharides, nucleic acids, carbohydrates, synthetic polymers, or mixtures thereof. In one embodiment, a biocompatible binder comprises collagen. In another embodiment, a biocompatible binder comprises collagen, such as bovine or human collagen.

The present invention additionally provides methods of producing compositions for the reattachment of tendons to bone, the strengthening of tendon attachment to bone, and/or the treatment of tendons including, but not limited to, those associated with rotator cuff tears. In one embodiment, a method for producing a composition comprises providing a solution comprising PDGF, providing a biocompatible matrix, and disposing the solution in the biocompatible matrix.

The present invention also provides methods for the reattachment of tendons to bone, the strengthening of tendon attachment to bone as well as methods for the treatment of tendons including damaged or injured tendons, such as those exhibiting tearing, delamination, or any other strain or deformation. In one embodiment, a method for attaching a tendon to bone and/or strengthening tendon attachment to bone comprises providing a composition comprising a PDGF solution disposed in a biocompatible matrix and applying the composition to at least one site of tendon reattachment on the bone. In another embodiment, a method for treating rotator cuff tears comprises providing a composition comprising a PDGF solution disposed in a biocompatible matrix and applying the composition to at least one site of tendon reattachment on the humeral head. In some embodiments, a method for treating a rotator cuff tear further comprises disposing at least one bone anchor in the humeral head, the at least one bone anchor further comprising a PDGF solution disposed in a biocompatible matrix, and coupling at least one detached tendon to the bone anchor.

In another embodiment, a method of treating a tendon comprises providing a composition comprising a PDGF solution disposed in a biocompatible matrix and applying the composition to a surface of at least one tendon. In some embodiments, the at least one tendon is an injured or damaged tendon, such as tendon exhibiting tearing, delamination, or any other deformation.

In some embodiments, the present invention may be used to repair a tendon tear that is not at a bone attachment point. Such a tendon tear may be sutured together with an overlay material which would release PDGF from the material. In some embodiments, for example, a tear occurs in midsubstance ruptures of the Achilles Tendon. Overlay materials for treating and/or repairing a tendon tear not at a point of bone attachment, in some embodiments, comprise biocompatible matrices including, but not limited to, fibrous collagen matrices, crosslinked hyaluron, allograft tissue, other synthetic matrices or combinations thereof.

In another aspect, the present invention provides a kit comprising a solution comprising PDGF in a first container and a second container comprising a biocompatible matrix. In some embodiments, the solution comprises a predetermined concentration of PDGF. The concentration of PDGF, in some embodiments, can be predetermined according to the nature of the tendon being treated. The kit may further comprise a scaffolding material and the scaffolding material may further comprise a biocompatible binder. Moreover, the amount of biocompatible matrix provided by a kit can be dependent on the nature of the tendon being treated. Biocompatible matrix that may be included in the kit may be a scaffolding material, a scaffolding material and a biocompatible binder, and/or bone allograft such as DFDBA or particulate DBM. In one embodiment the bone scaffolding material comprises a calcium phosphate, such as β-TCP. In another embodiment, a scaffolding material comprises a type I collagen patch as described herein. A syringe, in some embodiments, can facilitate disposition of the PDGF solution in the biocompatible matrix for application at a surgical site, such as a site of tendon attachment to bone. The kit may also contain instructions for use.

Accordingly it is an object of the present invention to provide a composition comprising PDGF useful in the attachment of tendon to bone.

Accordingly, it is an object of the present invention to provide a composition comprising PDGF useful for repair of tendons.

It is another object of the present invention to provide a method for attachment of tendon to bone using a composition comprising PDGF.

Another object of the present invention is to provide a composition comprising PDGF and method of using this composition to attach rotator cuff tendons to the humerus.

Another object of the present invention is to provide a composition comprising PDGF disposed in a matrix and a method of using this composition to attach rotator cuff tendons to the humerus.

Another object of the present invention is to provide a composition comprising PDGF disposed in a matrix and further comprising a binder, and a method of using this composition to attach rotator cuff tendons to the humerus These and other embodiments of the present invention are described in greater detail in the detailed description which follows. These and other objects, features and advantages of the present invention will become apparent after a review of the following detailed description of the disclosed embodiments and claims.

DETAILED DESCRIPTION

Figure 1:
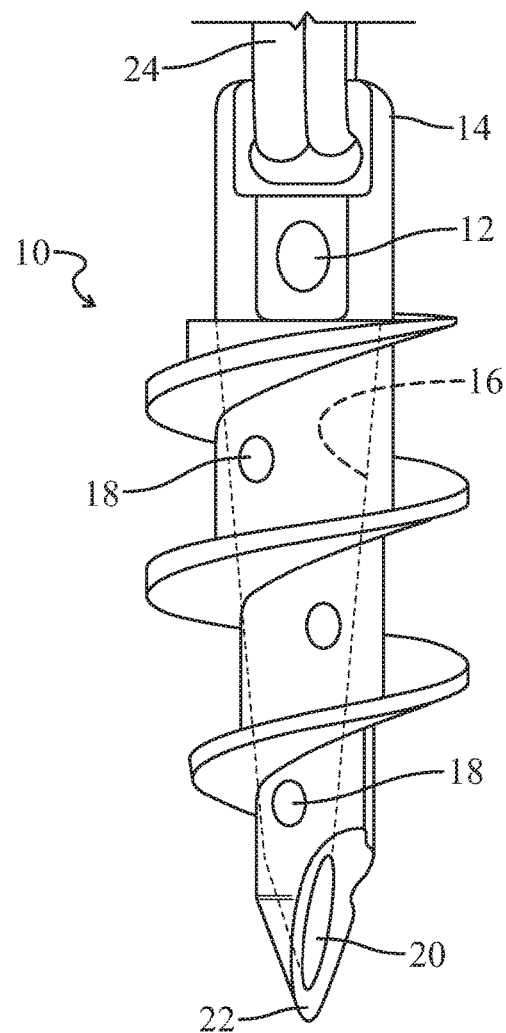
FIG. 1 illustrates a bone anchor according to an embodiment of the present invention.
Figure 2:
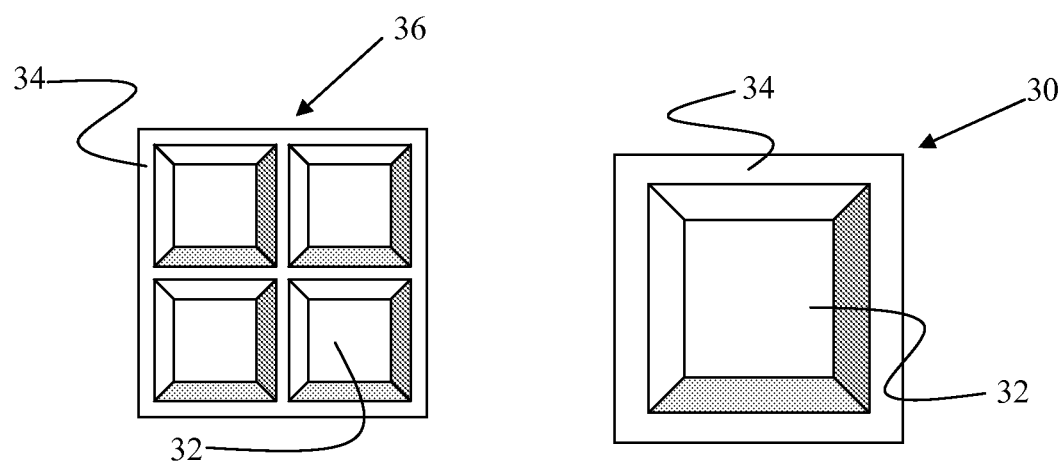
FIG. 2 illustrates two embodiments, 30 and 36, of an encapsulated PDGF composition, also showing a PDGF pouch 32 and a suturing border 34.

The present invention provides compositions and methods for the treatment and/or repair of damaged tendons. In some embodiments, compositions and methods of the present invention are useful in the attachment or reattachment of tendons to bone, and may be applied to any tendon reattachment. In some embodiments, compositions and methods of the present invention enhance tendon attachment to bone by strengthening the tendon and/or bone at the site of tendon attachment to the bone. Moreover, the treatment of tendons encompasses application of compositions of the present invention to tendons, including damaged or injured tendons, such as tendons exhibiting tearing, delamination, and/or any other strain or deformation. Tendons which may be reattached to bone and/or treated by compositions and methods of the present invention include, but are not limited to, tendons of the subscapularis, supraspinatus, infraspinatus, teres minor, rectus femoris, tibialis posterior, and quadraceps femoris, as well as the Achilles Tendon, patellar tendon, abductor and adductor tendons, or other tendons of the hip.

The present invention, in one embodiment, for example, provides compositions and methods for the treatment of rotator cuff tears. As used herein, rotator cuff tears include complete tendon detachment as well as incomplete or partial tendon detachment. The present compositions and methods facilitate the healing response to rotator cuff repairs and tendon reattachment to the humeral head.

In one embodiment, a composition for promoting tendon reattachment to bone, such as the humeral head, comprises a solution comprising PDGF and a biocompatible matrix, wherein the solution is disposed in the biocompatible matrix. In another embodiment, a composition comprises a PDGF solution disposed in a biocompatible matrix, wherein the biocompatible matrix comprises a bone scaffolding material and a biocompatible binder. In one aspect, biocompatible matrices may include calcium phosphate particles with or without biocompatible binders or bone allograft such as DFDBA or particulate DBM. In another aspect, biocompatible matrices may include DFDBA or DBM.

Turning now to components that can be included in various embodiments of the present invention, compositions of the present invention comprise a solution comprising PDGF.

PDGF Solutions

In one aspect, a composition provided by the present invention comprises a solution comprising platelet derived growth factor (PDGF) and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, from about 0.1 mg/ml to about 1.0 mg/ml. PDGF may be present in the solution at any concentration within these stated ranges. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; or about 1.0 mg/ml. It is to be understood that these concentrations are simply examples of particular embodiments, and that the concentration of PDGF may be within any of the concentration ranges stated above.

Various amounts of PDGF may be used in the compositions of the present invention. Amounts of PDGF that could be used include amounts in the following ranges: about 1 μg to about 50 mg, about 10 μg to about 25 mg, about 100 μg to about 10 mg, and about 250 μg to about 5 mg.

The concentration of PDGF or other growth factors in embodiments of the present invention can be determined by using an enzyme-linked immunoassay as described in U.S. Pat. Nos. 6,221,625, 5,747,273, and 5,290,708, or any other assay known in the art for determining PDGF concentration. When provided herein, the molar concentration of PDGF is determined based on the molecular weight of PDGF dimer (e.g., PDGF-BB; MW about 25 kDa).

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human PDGF, such as rhPDGF-BB.

PDGF, in some embodiments, can be obtained from natural sources. In other embodiments, PDGF can be produced by recombinant DNA techniques. In other embodiments, PDGF or fragments thereof may be produced using peptide synthesis techniques known to one of skill in the art, such as solid phase peptide synthesis. When obtained from natural sources, PDGF can be derived from biological fluids. Biological fluids, according to some embodiments, can comprise any treated or untreated fluid associated with living organisms including blood Biological fluids, in another embodiment, can also comprise blood components including platelet concentrate (PC), apheresed platelets, platelet-rich plasma (PRP), plasma, serum, fresh frozen plasma (FFP), and buffy coat (BC). Biological fluids, in a further embodiment, can comprise platelets separated from plasma and resuspended in a physiological fluid.

When produced by recombinant DNA techniques, a DNA sequence encoding a single monomer (e.g., PDGF B-chain or A-chain), in some embodiments, can be inserted into cultured prokaryotic or eukaryotic cells for expression to subsequently produce the homodimer (e.g. PDGF-BB or PDGF-AA). In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g. PDGF-AB). Commercially available cGMP recombinant PDGF-BB can be obtained commercially from Chiron Corporation (Emeryville, Calif.). Research grade rhPDGF-BB can be obtained from multiple sources including R&D Systems, Inc. (Minneapolis, Minn.), BD Biosciences (San Jose, Calif.), and Chemicon, International (Temecula, Calif.).

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with one embodiment, the rhPDGF-BB comprises at least 65% of intact rhPDGF-B (1-109). In accordance with other embodiments, the rhPDGF-BB comprises at least 75%, 80%, 85%, 90%, 95%, or 99% of intact rhPDGF-B (1-109).

In some embodiments of the present invention, PDGF can be purified. Purified PDGF, as used herein, comprises compositions having greater than about 95% by weight PDGF prior to incorporation in solutions of the present invention. The solution may be any pharmaceutically acceptable solution. In other embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into scaffolds and binders.

In a further embodiment, PDGF can be partially purified. Partially purified PDGF, as used herein, comprises compositions having PDGF in the context of PRP, FFP, or any other blood product that requires collection and separation to produce PDGF. Embodiments of the present invention contemplate that any of the PDGF isoforms provided herein, including homodimers and heterodimers, can be purified or partially purified. Compositions of the present invention containing PDGF mixtures may contain PDGF isoforms or PDGF fragments in partially purified proportions. Partially purified and purified PDGF, in some embodiments, can be prepared as described in U.S. patent application Ser. No. 11/159,533 (Publication No: 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethyl-piperazine-N'-2-ethanesulfonic acid (HEPES), and 3-(N-morpholino) propanesulfonic acid (MOPS). Buffers can be selected based on biocompatibility with PDGF and the buffer's ability to impede undesirable protein modification. Buffers can additionally be selected based on compatibility with host tissues. In one embodiment, sodium acetate buffer is used. The buffers may be employed at different molarities, for example about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM.

In another embodiment, solutions comprising PDGF are formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In one embodiment, a solution comprising PDGF has a pH ranging from about 5.0 to about 8.0, more preferably about 5.5 to about 7.0, most preferably about 5.5 to about 6.5, or any value within these ranges. The pH of solutions comprising PDGF, in some embodiments, can be compatible with the prolonged stability and efficacy of PDGF or any other desired biologically active agent. PDGF is generally more stable in an acidic environment. Therefore, in accordance with one embodiment the present invention comprises an acidic storage formulation of a PDGF solution. In accordance with this embodiment, the PDGF solution preferably has a pH from about 3.0 to about 7.0, and more preferably from about 4.0 to about 6.5. The biological activity of PDGF, however, can be optimized in a solution having a neutral pH range. Therefore, in a further embodiment, the present invention comprises a neutral pH formulation of a PDGF solution. In accordance with this embodiment, the PDGF solution preferably has a pH from about 5.0 to about 8.0, more preferably about 5.5 to about 7.0, most preferably about 5.5 to about 6.5. In accordance with a method of the present invention, an acidic PDGF solution is reformulated to a neutral pH composition, wherein such composition is then used to treat bone, ligaments, tendons or cartilage in order to promote their growth and/or healing. In accordance with a preferred embodiment of the present invention, the PDGF utilized in the solutions is rhPDGF-BB.

In some embodiments, the pH of the PDGF containing solution may be altered to optimize the binding kinetics of PDGF to a matrix substrate or linker. If desired, as the pH of the material equilibrates to adjacent material, the bound PDGF may become labile.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis(beta-aminoethylether)-N,N,N',N'-tetraacetic acid (EGTA), aprotinin, ϵ-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), bone morphogenetic proteins (BMPs), or other PDGFs including compositions of PDGF-AA, PDGF-BB, PDGF-AB, PDGF-CC and/or PDGF-DD.

In addition to solutions comprising PDGF, compositions of the present invention also comprise a biocompatible matrix in which to dispose the PDGF solutions and may also comprise a biocompatible binder either with or without a biocompatible matrix.

Biocompatible Matrix

Scaffolding Material

A biocompatible matrix, according to embodiments of the present invention, comprises a scaffolding material. The scaffolding material, according to embodiments of the present invention, provides a framework or scaffold for new tissue growth to occur, including tendon and/or bone tissue. A scaffolding material, in some embodiments, comprises at least one calcium phosphate. In other embodiments, a scaffolding material can comprise a plurality of calcium phosphates. Calcium phosphates suitable for use as a scaffolding material, in embodiments of the present invention, have a calcium to phosphorus atomic ratio ranging from 0.5 to 2.0. In some embodiments the biocompatible matrix comprises an allograft such as DFDBA or particulate DBM.

Non-limiting examples of calcium phosphates suitable for use as bone scaffolding materials comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-TCP, hydroxyapatite (OHAp), poorly crystalline hydroxyapatite, tetracalcium phosphate (TTCP), heptacalcium decaphosphate, calcium metaphosphate, calcium pyrophosphate dihydrate, carbonated calcium phosphate, and calcium pyrophosphate.

Moreover, in some embodiments, a scaffolding material comprises a collagen patch or pad. A collagen patch or pad, in one embodiment of the present invention, comprises a fibrous collagen such as soluble type I bovine collagen. Fibrous collagen suitable for use in collagen patches or pads demonstrate sufficient mechanical properties, including wet tensile strength, to withstand suturing and hold a suture without tearing. In one embodiment, a collagen patch or pad has a density ranging from about 0.75 g/cm$^3$ to about 1.5 g/cm$^3$. Additionally, a collagen patch or pad for use in some embodiments of the present invention is porous and operable to absorb water in an amount ranging from about 1× to about 15× the mass of the collagen patch.

In some embodiments, a scaffolding material comprises porous structure. Porous bone scaffolding materials, according to some embodiments, can comprise pores having diameters ranging from about 1 μm to about 1 mm. In one embodiment, a scaffolding material comprises macropores having diameters ranging from about 100 μm to about 1 mm. In another embodiment, a scaffolding material comprises mesopores having diameters ranging from about 10 μm to about 100 μm. In a further embodiment, a scaffolding material comprises micropores having diameters less than about 10 μm. Embodiments of the present invention contemplate scaffolding materials comprising macropores, mesopores, and micropores or any combination thereof.

A porous scaffolding material, in one embodiment, has a porosity greater than about 25%. In another embodiment, a porous scaffolding material has a porosity greater than about 50%. In a further embodiment, a porous scaffolding material has a porosity greater than about 90%.

In some embodiments, a scaffolding material comprises a plurality of particles. A scaffolding material, for example, can comprise a plurality of calcium phosphate particles. Scaffolding particles, in one embodiment, have an average diameter ranging from about 1 μm to about 5 mm. In other embodiments, particles have an average diameter ranging from about 250 μm to about 750 μm. Scaffolding particles, in another embodiment, can have average diameter ranging from about 100 μm to about 400 μm. In a further embodiment, the particles have an average diameter ranging from about 75 μm to about 300 μm. In additional embodiments, scaffolding particles have an average diameter less than about 1 μm and, in some cases, less than about 1 mm.

Scaffolding materials, according to some embodiments, can be provided in a shape suitable for implantation (e.g., a sphere, a cylinder, or a block). In other embodiments, bone scaffolding materials are moldable, extrudable, and/or injectable. Moldable scaffolding materials can facilitate efficient placement of compositions of the present invention in and around tendons and/or bone, including sites of tendon attachment to bone. In some embodiments, moldable scaffolding materials are applied to bone and/or tendons with a spatula or equivalent device. In some embodiments, scaffolding materials are flowable. Flowable scaffolding materials, in some embodiments, can be applied to tendon reattachment sites through a syringe and needle or cannula. In some embodiments, the flowable scaffolding materials can be applied to sites of tendon reattachment percutaneously. In other embodiments, flowable scaffolding materials can be applied to a surgically exposed site of tendon reattachment. In a further embodiment, moldable and/or flowable scaffolding materials can be applied to bone anchors used in the reattachment of a tendon to a bone.

In some embodiments, scaffolding materials are bioresorbable. A scaffolding material, in one embodiment, can be resorbed within one year of in vivo implantation. In another embodiment, a scaffolding material can be resorbed within 1, 3, 6, or 9 months of in vivo implantation. Bioresorbability is dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Scaffolding Comprising β-Tricalcium Phosphate (β-TCP)

A scaffolding material for use as a biocompatible matrix, in some embodiments, comprises β-TCP. β-TCP, according to some embodiments, can comprise a porous structure having multidirectional and interconnected pores of varying diameters. In some embodiments, β-TCP comprises a plurality of pockets and non-interconnected pores of various diameters in addition to the interconnected pores. The porous structure of β-TCP, in one embodiment, comprises macropores having diameters ranging from about 100 μm to about 1 mm, mesopores having diameters ranging from about 10 μm to about 100 μm, and micropores having diameters less than about 10 μm. Macropores and micropores of the β-TCP can facilitate tissue in-growth including osteoinduction and osteoconduction while macropores, mesopores and micropores can permit fluid communication and nutrient transport to support tissue and bone regrowth throughout the β-TCP biocompatible matrix.

In comprising a porous structure, β-TCP, in some embodiments, can have a porosity greater than 25%. In other embodiments, β-TCP can have a porosity greater than 50%. In a further embodiment, β-TCP can have a porosity greater than 90%.

In some embodiments, a bone scaffolding material comprises β-TCP particles. β-TCP particles, in one embodiment, have an average diameter ranging from about 1 μm to about 5 mm. In other embodiments, β-TCP particles have an average diameter ranging from about 250 μm to about 750 μm. In another embodiment, β-TCP particles have an average diameter ranging from about 100 μm to about 400 μm. In a further embodiment, β-TCP particles have an average diameter ranging from about 75 μm to about 300 μm. In additional embodiments, β-TCP particles have an average diameter less than 25 μm and, in some cases, sizes less than 1 mm.

A biocompatible matrix comprising a β-TCP scaffolding material, in some embodiments, is provided in a shape suitable for implantation (e.g., a sphere, a cylinder, or a block). In other embodiments, a β-TCP scaffolding material is moldable, extrudable, and/or flowable thereby facilitating application of the matrix in areas of tendon reattachment, such as channels in the humeral head. Flowable matrices may be applied through syringes, tubes, or spatulas. In some embodiments, moldable, extrudable, and/or flowable β-TCP scaffolding materials are applied to bone anchors used in the reattachment of tendons to bone.

A β-TCP scaffolding material, according to some embodiments, is bioresorbable. In one embodiment, a β-TCP scaffolding material can be at least 75% resorbed one year subsequent to in vivo implantation. In another embodiment, a β-TCP bone scaffolding material can be greater than 90% resorbed one year subsequent to in vivo implantation.

Scaffolding Material Comprising a Collagen Patch

In some embodiments, a scaffolding material comprises a collagen patch or pad. A collagen patch or pad, in one embodiment of the present invention, comprises a fibrous collagen such as soluble type I bovine collagen. In another embodiment, a fibrous collagen comprises type II or type III collagen. Fibrous collagen suitable for use in collagen patches or pads demonstrate sufficient mechanical properties, including wet tensile strength, to withstand suturing and hold a suture without tearing. A fibrous collagen patch, for example, can have a wet tear strength ranging from about 0.75 pounds to about 5 pounds. In one embodiment, a collagen patch or pad has a density ranging from about 0.75 g/cm$^3$ to about 1.5 g/cm$^3$. Additionally, a collagen patch or pad for use in some embodiments of the present invention is porous and operable to absorb water in an amount ranging from about 1× to about 15× the mass of the collagen patch.

Scaffolding Material and Biocompatible Binder

In another embodiment, a biocompatible matrix comprises a scaffolding material and a biocompatible binder. Biocompatible matrices comprising a scaffolding material and a biocompatible binder, according to embodiments of the present invention, are useful for the repair, strengthening, and/or reattachment of tendons to bone by providing a structure for new tendon and/or bone tissue growth.

Biocompatible binders, according to some embodiments, can comprise materials operable to promote cohesion between combined substances. A biocompatible binder, for example, can promote adhesion between particles of a bone scaffolding material in the formation of a biocompatible matrix. In certain embodiments, the same material may serve as both a scaffolding material and a binder if such material acts to promote cohesion between the combined substances and provides a framework for new tissue growth to occur, including tendon and bone growth.

Biocompatible binders, in some embodiments, can comprise collagen, elastin, polysaccharides, nucleic acids, carbohydrates, proteins, polypeptides, poly(α-hydroxy acids), poly(lactones), poly(amino acids), poly(anhydrides), polyurethanes, poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate),polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly (ethylene terephthalate)polyamide, and copolymers and mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, lecithin, phosphatidylcholine derivatives, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, a pluronic acids, sodium glycerophosphate, glycogen, a keratin, silk, and derivatives and mixtures thereof.

In some embodiments, a biocompatible binder is water-soluble. A water-soluble binder can dissolve from the biocompatible matrix shortly after its implantation, thereby introducing macroporosity into the biocompatible matrix. Macroporosity, as discussed herein, can increase the osteoconductivity of the implant material by enhancing the access and, consequently, the remodeling activity of the osteoclasts and osteoblasts at the implant site.

In some embodiments, a biocompatible binder can be present in a biocompatible matrix in an amount ranging from about 5 weight percent to about 50 weight percent of the matrix. In other embodiments, a biocompatible binder can be present in an amount ranging from about 10 weight percent to about 40 weight percent of the biocompatible matrix. In another embodiment, a biocompatible binder can be present in an amount ranging from about 15 weight percent to about 35 weight percent of the biocompatible matrix. In a further embodiment, a biocompatible binder can be present in an amount of about 20 weight percent of the biocompatible matrix.

A biocompatible matrix comprising a scaffolding material and a biocompatible binder, according to some embodiments, can be flowable, moldable, and/or extrudable. In such embodiments, a biocompatible matrix can be in the form of a paste or putty. A biocompatible matrix in the form of a paste or putty, in one embodiment, can comprise particles of a scaffolding material adhered to one another by a biocompatible binder.

A biocompatible matrix in paste or putty form can be molded into the desired implant shape or can be molded to the contours of the implantation site. In one embodiment, a biocompatible matrix in paste or putty form can be injected into an implantation site with a syringe or cannula. In a further embodiment, moldable and/or flowable scaffolding materials can be applied to bone anchors used in the reattachment of a tendon to a bone.

In some embodiments, a biocompatible matrix in paste or putty form does not harden and retains a flowable and moldable form subsequent to implantation. In other embodiments, a paste or putty can harden subsequent to implantation, thereby reducing matrix flowability and moldability.

A biocompatible matrix comprising a scaffolding material and a biocompatible binder, in some embodiments, can also be provided in a predetermined shape including a block, sphere, or cylinder or any desired shape, for example a shape defined by a mold or a site of application.

A biocompatible matrix comprising a scaffolding material and a biocompatible binder, in some embodiments, is bioresorbable. A biocompatible matrix, in such embodiments, can be resorbed within one year of in vivo implantation. In another embodiment, a biocompatible matrix comprising a bone scaffolding material and a biocompatible binder can be resorbed within 1, 3, 6, or 9 months of in vivo implantation. Bioresorbablity, in some embodiments, is dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated;

and (6) the use of other materials in addition to the matrix such as other bone anabolic, catabolic and anti-catabolic factors.

Biocompatible Matrix Comprising β-TCP and Collagen

In some embodiments, a biocompatible matrix can comprise a β-TCP scaffolding material and a biocompatible collagen binder. β-TCP scaffolding materials suitable for combination with a collagen binder are consistent with those provided hereinabove.

A collagen binder, in some embodiments, comprises any type of collagen, including Type I, Type II, and Type III collagens. In one embodiment, a collagen binder comprises a mixture of collagens, such as a mixture of Type I and Type II collagen. In other embodiments, a collagen binder is soluble under physiological conditions. Other types of collagen present in bone or musculoskeletal tissues may be employed. Recombinant, synthetic and naturally occurring forms of collagen may be used in the present invention.

A biocompatible matrix, according to some embodiments, comprises a plurality of β-TCP particles adhered to one another with a collagen binder. In one embodiment, β-TCP particles suitable for combination with a collagen binder have an average diameter ranging from about 1 µm to about 5 mm. In another embodiment, β-TCP particles suitable for combination with a collagen binder have an average diameter ranging from about 1 µm to about 1 mm. In other embodiments, β-TCP particles have an average diameter ranging from about 200 µm to about 3 mm or about 200 µm to about 1 mm, or about 1 mm to about 2 mm. In some embodiments, β-TCP particles have an average diameter ranging from about 250 µm to about 750 µm. β-TCP particles, in other embodiments, have an average diameter ranging from about 100 µm to about 400 µm. In a further embodiment, β-TCP particles have an average diameter ranging from about 75 µm to about 300 µm. In additional embodiments, β-TCP particles have an average diameter less than about 25 µm and, in some cases, less than about 1 mm. β-TCP particles, in some embodiments, can be adhered to one another by the collagen binder so as to produce a biocompatible matrix having a porous structure. In some embodiments, a biocompatible matrix comprising β-TCP particles and a collagen binder can comprise pores having diameters ranging from about 1 µm to about 1 mm. A biocompatible matrix comprising β-TCP particles and a collagen binder can comprise macropores having diameters ranging from about 100 µm to about 1 mm, mesopores having diameters ranging from about 10 µm to 100 µm, and micropores having diameters less than about 10 µm.

A biocompatible matrix comprising β-TCP particles and a collagen binder can have a porosity greater than about 25%. In another embodiment, the biocompatible matrix can have a porosity greater than about 50%. In a further embodiment, the biocompatible matrix can have a porosity greater than about 90%.

A biocompatible matrix comprising β-TCP particles, in some embodiments, can comprise a collagen binder in an amount ranging from about 5 weight percent to about 50 weight percent of the matrix. In other embodiments, a collagen binder can be present in an amount ranging from about 10 weight percent to about 40 weight percent of the biocompatible matrix. In another embodiment, a collagen binder can be present in an amount ranging from about 15 weight percent to about 35 weight percent of the biocompatible matrix. In a further embodiment, a collagen binder can be present in an amount of about 20 weight percent of the biocompatible matrix.

A biocompatible matrix comprising β-TCP particles and a collagen binder, according to some embodiments, can be flowable, moldable, and/or extrudable. In such embodiments, the biocompatible matrix can be in the form of a paste or putty. A paste or putty can be molded into the desired implant shape or can be molded to the contours of the implantation site. In one embodiment, a biocompatible matrix in paste or putty form comprising β-TCP particles and a collagen binder can be injected into an implantation site with a syringe or cannula. In a further embodiment, moldable, extrudable, and/or flowable matrix comprising β-TCP particles and a collagen binder can be applied to bone anchors and/or sutures used in the reattachment of a tendon to a bone.

In some embodiments, a biocompatible matrix in paste or putty form comprising β-TCP particles and a collagen binder can retain a flowable and moldable form when implanted. In other embodiments, the paste or putty can harden subsequent to implantation, thereby reducing matrix flowability and moldability.

A biocompatible matrix comprising β-TCP particles and a collagen binder, in some embodiments, can be provided in a predetermined shape such as a block, sphere, or cylinder.

A biocompatible matrix comprising β-TCP particles and a collagen binder can be resorbable. In one embodiment, a biocompatible matrix comprising β-TCP particles and a collagen binder can be at least 75% resorbed one year subsequent to in vivo implantation. In another embodiment, a biocompatible matrix comprising β-TCP particles and a collagen binder can be greater than 90% resorbed one year subsequent to in vivo implantation.

In some embodiments, a solution comprising PDGF can be disposed in a biocompatible matrix to produce a composition for the treatment of rotator cuff tears.

Disposing PDGF Solution in a Biocompatible Matrix

In another aspect, the present invention provides methods for producing compositions for use in the treatment of damaged or injured tendons, including those associated with torn rotator cuffs. In one embodiment, a method for producing such compositions for the treatment of tendons and/or bone comprises providing a solution comprising PDGF, providing a biocompatible matrix, and disposing the solution in the biocompatible matrix. PDGF solutions and biocompatible matrices suitable for combination are consistent with those described hereinabove.

In some embodiments, a PDGF solution can be disposed in a biocompatible matrix by soaking the biocompatible matrix in the PDGF solution. A PDGF solution, in another embodiment, can be disposed in a biocompatible matrix by injecting the biocompatible matrix with the PDGF solution. In some embodiments, injecting a PDGF solution can comprise disposing the PDGF solution in a syringe and expelling the PDGF solution into the biocompatible matrix to saturate the biocompatible matrix.

The biocompatible matrix, according to some embodiments, can be in a predetermined shape, such as a brick or cylinder, prior to receiving a PDGF solution. Subsequent to receiving a PDGF solution, the biocompatible matrix can have a paste or putty form that is flowable, extrudable, and/or injectable. In other embodiments, the biocompatible matrix can already demonstrate a flowable paste or putty form prior to receiving a solution comprising PDGF.

Compositions Further Comprising Biologically Active Agents

Compositions of the present invention, according to some embodiments, further comprise one or more biologically active agents in addition to PDGF. Biologically active agents that can be incorporated into compositions of the present invention, in addition to PDGF, can comprise organic molecules, inorganic materials, proteins, peptides, nucleic acids (e.g., genes, gene fragments, small-insert ribonucleic acids [si-RNAs], gene regulatory sequences, nuclear transcriptional factors and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. patent application Ser. No. 11/159,533 (Publication No: 20060084602). Biologically active compounds that can be incorporated into compositions of the present invention, in some embodiments, include osteoinductive factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, calcitonin mimetics, statins, statin derivatives, fibroblast growth factors, insulin-like growth factors, growth differentiating factors, and/or parathyroid hormone. Additional factors for incorporation into compositions of the present invention, in some embodiments, include protease inhibitors, as well as osteoporotic treatments that decrease bone resorption including bisphosphonates, and antibodies to the NF-kB (RANK) ligand.

Standard protocols and regimens for delivery of additional biologically active agents are known in the art. Additional biologically active agents can introduced into compositions of the present invention in amounts that allow delivery of an appropriate dosage of the agent to the damaged tendon and/or the site of tendon reattachment. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition for the treatment of tendons and/or bone, according to some embodiments, further comprises other bone grafting materials with PDGF including autologous bone marrow, autologous platelet extracts, allografts, synthetic bone matrix materials, xenografts, and derivatives thereof.

Methods of Treating and Reattaching Tendons

The present invention also provides methods for the attachment or reattachment of tendons to bone, the strengthening of tendon attachment to bone as well as the treatment of tendons, such as tendons exhibiting tearing, delamination, or any other strain or deformation. In one embodiment, a method for reattaching a tendon to bone comprises providing a composition comprising a PDGF solution disposed in a biocompatible matrix and applying the composition to at least one site of tendon reattachment on the bone. In another embodiment, a method of strengthening the attachment of a tendon to a bone comprises providing a composition comprising a PDGF solution disposed in a biocompatible matrix and applying the composition to at least one site of tendon attachment to bone. Methods of strengthening tendon attachment to bone, in some embodiments, assist in preventing or inhibiting tendon detachment from bone, such as in rotator cuff injuries.

The present invention also provides methods of treating rotator cuff tears. In one embodiment, a method for treating rotator cuff tears comprises providing a composition comprising a PDGF solution disposed in a biocompatible matrix and applying the composition to at least one site of tendon reattachment on the humeral head. In some embodiments, applying the composition to at least one site of tendon reattachment can comprise molding the composition to the contours of the reattachment site on the humeral head. A composition, for example, can be molded into a channel formed on a surface of the humeral head for receiving the detached tendon. The composition may be applied to the vicinity of the insertion site of the tendon into bone to further strengthen the attachment.

In some embodiments, a method for treating rotator cuff tears further comprises disposing at least one anchoring means, such as a bone anchor in the humeral head, wherein the bone anchor further comprises a PDGF composition, and coupling at least one detached tendon to the bone anchor. In embodiments of the present invention, tendons can be secured to bone anchors through sutures. Sutures may also be soaked in PDGF solutions or coated in PDGF compositions before use. Examples 2-4 describe three different methods for treating rotator cuff tears.

In another embodiment, a method of treating a tendon comprises providing a composition comprising a PDGF solution disposed in a biocompatible matrix and applying the composition to a surface of at least one tendon. In some embodiments, the at least one tendon is an injured or damaged tendon, such as tendon exhibiting tearing, delamination, or any other deformation.

PDGF solutions and biocompatible matrices suitable for use in compositions, according to embodiments of methods of the present invention, are consistent with those provided hereinabove.

Kits

In another aspect, the present invention provides a kit comprising a solution comprising PDGF in a first container and a second container comprising a biocompatible matrix. In some embodiments, the solution comprises a predetermined concentration of PDGF. The concentration of PDGF, in some embodiments, can be predetermined according to the nature of the tendon being treated. The kit may further comprise a scaffolding material and the scaffolding material may further comprise a biocompatible binder. Moreover, the amount of biocompatible matrix provided by a kit can be dependent on the nature of the tendon being treated. Biocompatible matrix that may be included in the kit may be a scaffolding material, a scaffolding material and a biocompatible binder, and/or bone allograft such as DFDBA or particulate DBM. In one embodiment the bone scaffolding material comprises a calcium phosphate, such as β-TCP. In another embodiment, a scaffolding material comprises a type I collagen patch as described herein. A syringe, in some embodiments, can facilitate disposition of the PDGF solution in the biocompatible matrix for application at a surgical site, such as a site of tendon attachment to bone. The kit may also contain instructions for use.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of a Composition Comprising a Solution of PDGF and a Biocompatible Matrix A composition comprising a solution of PDGF and a biocompatible matrix was prepared according to the following procedure.

A pre-weighed block of biocompatible matrix comprising β-TCP and collagen was obtained. The β-TCP comprised pure β-TCP particles having sizes ranging from about 75 μm to about 300 μm. The β-TCP particles were formulated with approximately 20% weight percent soluble bovine collagen binder. A β-TCP/collagen biocompatible matrix can be commercially obtained from Kensey Nash (Exton, Pa.).

A solution comprising rhPDGF-BB was obtained. rhPDGF-BB is commercially available from Chiron Corporation at a stock concentration of 10 mg/ml (i.e., Lot #QA2217) in a sodium acetate buffer. The rhPDGF-BB is produced in a yeast expression system by Chiron Corporation and is derived from the same production facility as the rhPDGF-BB that is utilized in the products REGRANEX, (Johnson &Johnson) and GEM 21S (BioMimetic Therapeutics) which has been approved for human use by the United States Food and Drug Administration. This rhPDGF-BB is also approved for human use in the European Union and Canada. The rhPDGF-BB solution was diluted to 0.3 mg/ml in the acetate buffer. The rhPDGF-BB solution can be diluted to any desired concentration according to embodiments of the present invention.

A ratio of about 91 μl of rhPDGF-BB solution to about 100 mg dry weight of the β-TCP/collagen biocompatible matrix was used to produce the composition. The rhPDGF-BB solution was expelled on the biocompatible matrix with a syringe, and the resulting composition was blended and molded into a thin strand for insertion into a 1 cc tuberculin syringe for placement at a site of tendon reattachment.

EXAMPLE 2

Treating Rotator Cuff Tears with an Open Repair Method

Open repair is performed without arthroscopy, and is typically used for larger rotator cuff injuries. In accordance with this method of the present invention, a surgeon makes a two- to three-inch incision over the shoulder and separates the deltoid muscle from the anterior acromion to gain access to and improve visualization of the torn rotator cuff. The deltoid muscle should only be detached to the extent necessary to gain sufficient access to the rotator cuff injury. Following the rotator cuff repair procedure, the deltoid is repaired with sutures to close the longitudinal divisional of the muscle.

The surgeon then identifies the detached end of the involved tendon(s) (infraspinatus, supraspinatus, teres minor, and/or subscapularis) and the remaining tendon stump is cut away or removed from the humeral head preferably with a rasp, rongeur, scalpel or high speed bur and/or shaver. The surgeon may perform an acromioplasty (removal of bone spurs from the undersurface of the acromion) and remove any scar tissue that has built up on the tendon. Following debridement, cortical bone of the humeral head is abraded so as to produce bleeding bone and provide access for migrating mesenchymal stem cells of the bone marrow. In accordance with one embodiment of the method of the present invention, the cortical bone is removed so as to form a small channel in the humeral head that corresponds in shape and size to the original tendon attachment footprint. Preferably the channel is formed adjacent to the articular cartilage of the shoulder joint.

Prior to reattachment of the tendon, the surgeon may drill small holes within the channel through the bone. These holes may be used to affix bone anchors (preferably bone anchor screws). The bone anchors may be formed from any biocompatible material, and are preferably made of either a biocompatible metal or a resorbable composition. In accordance with an embodiment of the invention, bone anchor screws are affixed in a double row arrangement. The anchors thereby become an attachment point used to affix sutures to the humeral head.

A pilot hole is first drilled prior to insertion of the anchors. A PDGF composition in accordance with the present invention is then put into the pilot hole prior to insertion of the anchor. In one embodiment, injectable forms of the PDGF composition of the present invention are injected into the pilot holes.

As shown in FIG. 1, in an alternative embodiment, a self-tapping self-drilling cannulated anchor 10 is used without the use of an initial pilot hole. Anchor 10 includes a needle access port 12 at or near its proximal end 14, a central channel 16 extending along the axis of anchor 10, and one or more exit ports, including radial exit ports 18 along the axis of anchor 10, and/or a distal exit port 20 located near the distal end 22 of anchor 10. In one embodiment, anchor 10 is drilled into the channel. Preferably a plurality of anchors 10 are used. Once inserted into the humeral head, a needle is inserted into the needle access port 12 of anchor 10, and a PDGF composition of the present invention is injected into the central channel 16. A sufficient amount of PDGF composition is injected into the anchor such that the PDGF composition fills the central channel 16 and flows out of the radial exit ports 18 and/or distal exit port 20 and into the surrounding bone. Any effective amount or concentration of PDGF composition may be used. In one embodiment, approximately 0.1 to 1.0 cc of a composition having approximately 0.3 to 1 mg/ml of PDGF is injected into each anchor or pilot hole.

In accordance with an embodiment of the present invention, the exit ports included in anchor 10 may be of varying diameter in order to regulate the rate at which the PDGF migrates into the surrounding bone. In addition, the rate of PDGF release within the surrounding bone is regulated by utilizing different PDGF formulations in the various anchors inserted into the channel. For example, the rate of PDGF release is prolonged by using more viscous compositions in certain anchors, or by using PDGF compositions comprising a matrix with extended PDGF release characteristics.

Alternatively, the drilled holes are used to affix sutures directly to the humeral head without the use of bone anchors.

In accordance with the next step of the method of the present invention, a PDGF composition is applied to substantially cover the channel. The PDGF composition used to cover the channel is in the form of either a solution, a putty, or a gel, as described herein above. Alternatively, the PDGF composition is in the form of a pad. The pad may be composed of a substrate that is hydrated with a PDGF solution. The substrate is made from fibrous type I collagen, collagen hydrogel, crosslinked hyaluronic acid, porcine small intestine submucosa (SIS), polylactic acid/polyglycolic acid, or cellulose.

After the channel is covered with the PDGF composition, the proximal end of the tendon is then placed over the PDGF composition and into the channel. The tendon is secured in place by use of sutures that pass through tendon, the PDGF composition and into bone or through the eyelets of the bone anchors. Any of the various standard suturing techniques known to those skilled in the art (e.g., Mason Allen, mattress, simple suturing) may be used.

In accordance with an embodiment, the sutures are also impregnated with a PDGF solution prior to use. The sutures may be soaked in or saturated with a PDGF composition. Any effective amount or concentration of PDGF composition may be used. In one embodiment, PDGF at concentrations of 0.1, 0.3, or 1.0 mg/mL may be used to wet the suture prior to use. Furthermore, the suture may be treated with glycerol, gelatin, or paraffin wax to slow the release of PDGF in a manner that is consistent with the wound healing process.

The PDGF composition may be applied adjacent to and/or over the tendon to augment healing of the tendon/bone margins. This PDGF composition may be in the form of a solution, putty, gel, or pad, and may be secured in position with the same sutures used to secure the tendon.

Following the implantation of the PDGF composition and suturing of the rotator cuff, all dissected muscles are sutured closed, the overlying fascia is repaired, and lastly the patient's skin is closed with sutures or staples.

EXAMPLE 3

Treating Rotator Cuff Tears with a Mini-Open Repair Method

A mini-open rotator cuff repair procedure involves using both an arthroscopic technique for part of the process in conjunction with a limited open technique typically done through a 3 cm to 5 cm incision. This technique also incorporates an arthroscopy to visualize the tear, assess and treat damage to other structures within the joint (i.e., labrum and remove the spurs under the acromion). Arthroscopic removal of spurs (acromioplasty) avoids the need to detach the deltoid muscle. Thereafter, an arthroscopic decompression may be performed. The decompression may be followed by a release and mobilization of the tendons and placement of tagging sutures. These steps may be done arthroscopically or open. The final steps are done in an open procedure, but via the smaller opening. In particular, a small lateral deltoid split is performed in order to place tendon-gripping sutures on the previously mobilized cuff and to fix the cuff to bone using either suture anchors or transosseous sutures.

In accordance with one embodiment, a mini-open repair method of the present invention comprises the following steps.

The patient is prepared in accordance with standard techniques for patient positioning and marking. The arthroscope is placed in the glenohumeral joint through the posterior portal and a thorough evaluation of the joint is performed. The rotator cuff tear is identified and a lateral portal is created.

Rotator cuff mobilization starts with an intra-articular release. A hooked electrocautery device is used to release the cuff from the glenoid labrum. This allows mobilization of the entire cuff if necessary (anterior to posterior). Once the intra-articular release has been performed, the arthroscope is directed to the subacromial space.

An arthroscopic subacromial bursectomy is performed. The tuberosity (area of rotator cuff insertion) is decorticated. In some applications the tuberosity may be only slightly decorticate with no formal channel being created. A shaver is used to debride any of the torn cuff edge that appears to be nonviable or attenuated. Stay sutures are placed in the edge of the cuff tear approximately 1 cm apart. The stay sutures may be pretreated with a PDGF composition in the manner described above in Example 2. Additional releases of the cuff from the glenoid are performed as necessary.

The mini-open approach is then initiated with a horizontal lateral incision (3-4 cm long) being made over the lateral edge of the acromion. The deltoid muscle fibers are split to expose the rotator cuff tear.

If the tear is small and easily mobilized, sutures are placed through the edge of the cuff tear which is then repaired using suture anchors placed in the superolateral aspect of the greater tuberosity. For large tears under some tension, special intratendinous sutures are placed through the cuff and these are then repaired using the suture anchors placed in the superolateral greater tuberosity. Prior to securing the cuff, a PDGF composition is placed between the tendon and the humeral head in the same manner as described above regarding open procedures. In addition, the sutures used to secure the tendon may be pretreated with PDGF in a manner similar to that described above. The suture anchors may be of the type described above and illustrated in FIG. 1. A PDGF composition may be injected into the suture anchors or into the suture anchor holes as described above. The surgery is completed in accordance with known closure techniques.

This arthroscopically assisted open repair has limitations when dealing with large or massive rotator cuff repairs. The necessary surgical releases can be difficult, if not impossible, to perform through a small trans-deltoid split. When compared to complete arthroscopic repair, the mini-open repair provides more secure bone-to-tendon fixation since tendon gripping sutures can be used.

EXAMPLE 4

Treating Rotator Cuff Tears with an All-Arthroscopic Repair Method

This technique uses multiple small incisions (portals) and arthroscopic technology to visualize and repair the rotator cuff. In addition, in accordance with the present invention this technique utilizes injectable or small encapsulated PDGF compositions that are capable of insertion through a keyhole incision or a cannula so that they are amenable to use with arthroscopic techniques.

In accordance with one embodiment, an arthroscopic repair method of the present invention comprises the following steps. The patient is prepared in accordance with standard techniques for patient positioning, assessment and marking. One or two very small (1 cm) incisions, or "portals" are made, preferably one in the front and one behind the shoulder joint. Through these small portals, hollow instruments called cannulae are placed that irrigate the inside of the shoulder joint with sterile saline and inflate the joint with clear fluid. The cannulae allow the placement of an arthroscopic camera and specially designed instruments within the shoulder joint. The surgeon inserts a camera into the joint and maneuvers the camera around the joint in order to perform diagnostic arthroscopy.

In the most common cases the diagnostic arthroscopy reveals that the supraspinatus tendon is torn and/or pulled back slightly from its normal attachment at the greater tuberosity of the humerus. These smaller tears which are non-retracted or minimally-retracted only need to be freshened or debrided back to stable, healthy tendon tissue, then mobilized back to the tuberosity and fixed in place. The surgeon utilizes suture anchors to hold the tear in position while it heals. As with anchors used in the procedures described in Example 2, these anchors can be made of metal or absorbable compounds. In addition, the anchors are be screwed or pressed into the bone of the attachment site and the attached sutures used to tie the edge of the rotator cuff in place.

Prior to securing the tendon, a protected PDGF composition is placed between the tendon and the humeral head. The material may be placed in the bone anchor holes as well as across the decorticated surface of the humeral head. In the event that the humeral head is not prepared by decortication, the PDGF composition is placed against the cortical bone of the humeral head, and the tendon sutured into place in a standard manner. The sutures used to secure the tendon may be impregnated with PDGF in a manner similar to that described above. The suture anchors may be of the type described above and illustrated in FIG. 1. An injectable PDGF composition may be injected into the suture anchors by inserting a needle through one of the cannula.

Figure 3A:
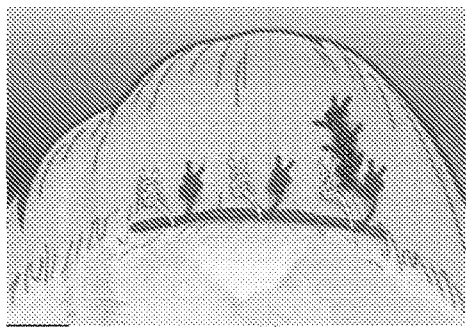
FIG. 3 illustrates a prior art technique (3A), a PDGF containing pad incorporated into sutures (3B), and a PDGF pouch sutured over a repaired tear (3C).
Figure 3B:
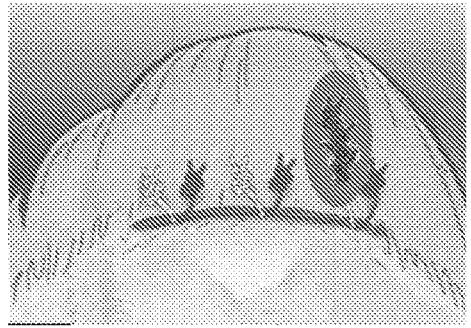
Figure 3C:
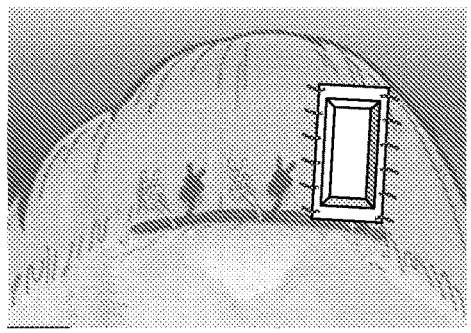

As tears become larger, they deform and the tendon tissue shrinks. Thus, larger tears need to be refashioned, repaired side-to-side, or zipped closed using a technique called margin convergence. This technique is analogous to zippering shut an open tent flap. The rotator cuff tissue is freed from a scarred, retracted position. A protected PDGF composition is then inserted through one of the cannula or directly through an incision. The protected PDGF composition comprises a PDGF composition as described herein above encapsulated in or otherwise associated with a membrane designed to protect the PDGF composition from the arthroscopic fluid environment of the surgical site (FIG. 3). The PDGF can be released at the treatment site using a variety of techniques to protect the protein during the initial placement to avoid rapid loss from the site due to the use of high volumes of fluids associated with the surgical procedure. In one embodiment, a membrane displays an intrinsic charge that promotes ionic interactions operable to release the PDGF in response to changing ionic conditions at the treatment or reattachment site. In another embodiment, a membrane forms a covalent interaction with the PDGF that is reversible via hydrolysis or enzymatic digestion to release the PDGF at the reattachment or treatment site. Membranes for protecting PDGF, in some embodiments, comprise collagen, polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, and copolymers and mixtures thereof. Additionally, the PDGF may be enclosed in ceramic materials such as tricalcium phosphate, hydroxyapatite, calcium sulphates, or variations thereof. In addition osmotic pumps may be used to provide protected release of the protein.

The protected PDGF composition is then placed over the tear and is sutured in place using the same sutures to do the side-to-side repair of the tear, and thereby restore the tissue over the top of the humeral head. A second protected PDGF composition is then inserted in the same manner as the first PDGF composition. The second protected PDGF composition is placed between the humeral head and the repaired cuff tissue. The repaired cuff tissue is then fixed to the site it originally tore away from preferably using suture anchors. The sutures are then sewn through the second protected PDGF composition and torn edge of the cuff to complete the repair.

At the conclusion of the procedure, any incisions are closed using absorbable or removable sutures. The patient's shoulder is placed into a postoperative sling to protect the shoulder during the early postoperative period.

Absorbable suture anchors or implants are gradually absorbed and the sutures attached are incorporated into the healing tissues. When metallic anchors are used (a matter of surgeon preference), these are buried in the bone, and do not affect the integrity of the bone or the shoulder joint.

EXAMPLE 5

Treatment of Rotator Cuff Injuries with β-TCP/PDGF Compositions

This study evaluated the efficacy of compositions comprising a rhPDGF-BB solution combined with a biocompatible matrix comprising β-tricalcium phosphate and type I collagen for the treatment and/or repair of rotator cuff injuries.

Study Design

Nine (9) adult female sheep were used in the present study. Six of the animals were administered a test composition comprising a 0.3 mg/ml rhPDGF-BB solution combined with a biocompatible matrix comprising β-tricalcium phosphate and type I collagen. As provided herein, 0.3 mg/ml rhPDGF-BB solutions was prepared by diluting stock rhPDGF-BB solutions with 20 mM sodium acetate buffer. The β-TCP was in particulate form, the particles having an average diameter ranging from about 75 μm to about 300 μm. Moreover, the type I collagen was present in an amount of about 20 weight percent of the biocompatible matrix. The remaining three animals were administered a control composition comprising a 20 mM solution of sodium acetate buffer combined with a biocompatible matrix comprising β-tricalcium phosphate and type I collagen.

As part of the study, the animals underwent a period (two weeks) of tendon detachment from the humerus, allowing degenerative changes to begin in the infraspinatus tendon. The degenerative changes were similar to those observed clinically in rotator cuff injuries. After two weeks, the animals underwent a tendon reattachment procedure in which the infraspinatus tendon was reattached to the humerus. As provided herein, six of the animals received the test composition at the site of tendon reattachment and the remaining three animals received the control composition at the site of tendon reattachment. All animals were allowed to heal for six weeks. At the six week point, all the animals were imaged with MRI. Subsequent to imaging, all the animals were humanely sacrificed and biomechanical analysis was performed on three of the animals receiving the test composition and three of the animals receiving the control composition.

Surgical Protocol

All animals were determined to be Q-fever negative prior to being placed in this study. Food was withheld from each animal 24 to 48 hours prior to the procedures and water was removed the morning of surgery. Each animal was given a general health evaluation (subject to visual observation for attitude, activity, and ease in respiration, freedom for diarrhea and nasal discharge) prior to being placed on the study. Respiratory infection, temperature elevations, observed depression, lameness or anatomical abnormality resulted in rejection of an individual animal from the surgical procedure. Each animal was weighed within 7 days prior to the procedure. Blood was collected for a CBC and Chemistry Profile within 7 days of surgery. Twelve animals were examined and all were found to be acceptable candidates for surgery.

Acepromazine maleate 0.075 mg/kg and Buprenorphine 0.005-0.01 mg/kg were administered im prior to anesthetic induction. An intravenous injection consisting of Diazepam 0.22 mg/kg and Ketamine 10 mg/kg was given for induction of general anesthesia. A cuffed endotracheal tube was placed and general anesthesia maintained with Isoflurane 0.5-5% delivered in oxygen through a rebreathing system. Each animal was placed on a ventilator to assist respiration. A catheter was placed in a peripheral ear vein of each animal. A stomach tube was placed if regurgitation occurred.

All surgical procedures were conducted utilizing routine aseptic techniques. Pre-operative preparation was conducted in the animal preparation room adjacent to the operating room. The appropriate shoulder and surrounding areas of each animal were prepared by clipping the area. Each animal was then moved to the operating room, and the area cleansed with chlorhexidine scrub alternating with 70% isopropyl alcohol three times and painted with iodine solution. Each animal was then draped for sterile surgery. Lactated Ringer's Solution (LRS) was intravenously infused at a rate of about 10-20 ml/kg/hr during surgery. Cefazolin 1-2 gram was intravenously administered prior to the initial incision, and 0.5g Cefazolin was placed in the flush solution for each surgery.

A. Tendon Detachment Surgical Procedure

A 15 cm curved incision was made over the posterolateral aspect of the shoulder joint. The incision was deepened, and the acromial portion of the deltoid muscle identified. The muscle was elevated at its cranial edge to expose the tendinous insertion of the infraspinatus muscle and its insertion into the proximal part of the humerus bone. The infraspinatus tendon was detached sharply from its insertion on the proximal humerus. The tendon was then wrapped in a 5 cm×3 cm sheet of PRECLUDE® (W.L. Gore & Associates, Newark, Del.). This allowed diffusion of nutrients to the tendon but inhibits scarring of the tendon to the surrounding tissues. The incision was closed in standard fashion. A 10 cm diameter softball was affixed to the hoof of the limb associated with the operation to inhibit weight bearing for 7 weeks post-operation. Cefazolin Ig was intravenously administered. A 100 μg fentanyl patch was placed on each animal.

B. Tendon Reattachment Surgical Procedure

Two weeks following initial surgery, each animal received a second procedure to repair the shoulder which underwent tendon detachment. The same surgical approach was used as in the first surgery.

In all animals, a moderate degree of tendon retraction was observed as well as adhesions to the tendon and muscle belly except for the region protected by PRECLUDE. These adhesions were dissected, freeing the muscle prior to reattachment in each animal. In preparation for insertion of bone anchors, the surface of the greater tuberosity was decorticated with a bone rongeur so as to create a bleeding bone surface and provide access to mesenchymal stem cell migration. At the same time, a 4 mm drill hole, approximately 10 mm deep was created within the decorticated area to provide a reservoir for test or control material. Two self-tapping suture anchors (15 mm in length by 5 mm wide) were then screwed into bone and on either side of the drill hole, and placed approximately 12 mm apart. Following insertion of the anchors, the tendon was unwrapped and mobilized by blunt dissection. The tendon was grasped with no. 2 ETHIBOND® (Johnson and Johnson) braided polyester suture in a modified Mason-Allen technique.

Prior to the reattachment surgery, stock PDGF-BB solutions (1.0 mg/mL, 5 mL total) (Lot #AAI-0022006-5A) were diluted 1:3 in 20 mM acetate buffer (pH 6.0) to a final concentration of about 0.3 mg/mL. The residual amounts of stock diluted PDGF-BB solutions were assayed by UV spectrophotometry to confirm the final solution concentration as provided in Table 1.

TABLE 1

Stock and diluted solutions of PDGF

| | PDGF Tube | OD | Stock Tube | Final Concentration (Undiluted) (0.53 Extinction Coefficient) |
|---|---|---|---|---|
| Final PDGF-BB Sample Dilutions | A | 0.125 | BMIG9 | 0.235849057 |
| | B | 0.188 | BMIG10 | 0.354716981 |
| | C | 0.207 | BMIG11 | 0.390566038 |
| | D | 0.187 | BMIG12 | 0.352830189 |
| | E | 0.173 | BMIG13 | 0.326415094 |
| | F | 0.181 | BMIG15 | 0.341509434 |
| | G | 0 | Acetate Buffer | 0 |
| | H | 0 | Acetate Buffer | 0 |
| | I | 0 | Saline** | 0 |
| Stock PDGF-BB Solutions | BMIG9 | 0.57 | N/A | 1.075471698 |
| | BMIG10 | 0.515 | N/A | 0.971698113 |
| | BMIG11 | 0.478 | N/A | 0.901886792 |
| | BMIG12 | 0.5 | N/A | 0.943396226 |
| | BMIG13 | 0.523 | N/A | 0.986792453 |
| | BMIG15 | 0.508 | N/A | 0.958490566 |

*Equation for determining protein concentration (OD*dilution factor)/0.53 = Final concentration (mg/mL)
**Saline was used to hydrate β-TCP/type I collagen matrix due to a shortage of acetate buffer Each animal received approximately 1 cc of a β-TCP/type I collagen matrix hydrated with either a 20 mM sodium acetate buffer solution (pH 6.0) or a 0.3 mg/mL rhPDGF-BB solution. For each animal, a fresh stock of acetate buffer or rhPDGF-BB stock solution was opened and diluted to produce the hydrating solution. Hydrating solutions A-I used in the preparation of compositions for the treatment of the nine animals in the study are provided in Table 1. Moreover, Table 2 provides the assignment of each of the hydrating solutions (A-I) to the animals in the study.

TABLE 2

Assignment schedule of control and test compositions

| Animal | Hydrating Solution | Applied dose of Test or Control Composition |
|---|---|---|
| G2437 | G | 1 cc |
| G1636 | A | 1 cc |
| G1637 | E | 1 cc |
| G1627 | F | 1 cc |
| G2923 | H | 1.5 cc |
| G2054 | I | 1 cc |
| G2051 | D | 1 cc |
| G1647 | C | 1 cc |
| G2922 | B | 1 cc |

Using aseptic technique, a 1 cc β-TCP/type I collagen brick was hydrated (1:3 ratio, β-TCP/type I collagen:PDGF solution) in a sterile dish with 3 cc of rhPDGF-BB solution or acetate buffer. In the case of hydrating solution "I", an insufficient volume of acetate buffer was available, and sterile saline was substituted for acetate buffer. The material was mixed with a sterile stainless spatula for approximately 1 minute until a homogenous consistency was achieved. The spatula was then used to load a 3 cc syringe barrel with as much of the test or control material as possible, the plunger inserted, and the graduated volume noted.

Approximately 1 cc of the test or control composition was applied across the bony tendon footprint and within the drill hole created between the anchors using a 3 cc syringe. Due to muscle and tendon wasting, and retraction, a modest amount of force was required to reapproximate the tendon anteriorly with its footprint. The tendon was then permanently tied to the anchor resting on bed of bleeding bone and test composition. For all animals, the process of suturing the tendon into place caused displacement of approximately 300 uL of the test or control composition into the space adjacent to the tendon. The wound was then closed in a standard fashion, and Cefazolin 1g iv was administered along with a 100 ug fentanyl dermal patch placed on each animal.

C. Post-Operative Care

The animals were returned to the pre/post operating room where postoperative monitoring was continued. In this environment, the animals were monitored during anesthetic recovery for physiological disturbances including cardiovascular/respiratory depression, hypothermia, and excessive bleeding from the surgical site. Supplemental heat was provided as needed. The endotracheal and stomach tubes were removed after the animals regained the swallow reflex and was breathing on their own. Cefazolin 1 gram and Buprenorphine 0.005-0.01 mg/kg were administered im once postoperatively as the last treatment of the day. Additional analgesic was given as deemed necessary by a staff veterinarian. Long term postoperative monitoring included inspection of surgical sites and return to normal physiological function and attitude. Each animal received im injections of antibiotics once daily for 3 days (Naxcel). Each animal was monitored and scored for pain daily for at least 5 days. Pain evaluation was according to The Assessment of Pain in Sheep and Goats after Orthopedic Surgery. Body temperature, pulse, and respiration were recorded for each animal on days 1-3. General health assessments were conducted daily for at least 14 days. After that time, animal health was monitored and changes to health status were noted. The same pre and post operative procedures were followed for both of the surgeries. The softball/casts were changed once during the duration of the study at four weeks after the first surgery. Seven weeks after the initial surgery (five weeks after the second), the softball was removed from the operative limb and the animals were allowed full movement of the leg.

Magnetic Resonance Imaging

Prior to the terminal procedure, all animals were imaged with a GE Healthcare Signa Hdx 1.5T MR imaging system on the operated shoulder. In both axial and coronal orientations, the animals were scanned first using a T1 weighted protocol, and second a T2 fat-suppressed protocol. Table 3 provides the imaging orientation and protocol for each animal.

TABLE 3

Imaging orientation and protocol

| Orientation | Protocol |
|---|---|
| T1 Axial | FSE-XL, 16 FoV, 3 mm slice thickness, 0.5 mm slice gap, 256 × 192 × Z512 matrix, 2 Nex, 8.8 TE, 600TR |
| STIR Axial | FSE-XL, 16 FoV, 3 mm slice thickness, 0.5 mm slice gap, 256 × 192 × Z512 matrix, 3 Nex, 60 TE, 4500 TR, 150 IR |
| T1 Coronal | FSE-XL, 16 FoV, 3 mm slice thickness, 0.5 mm slice gap, 256 × 192 × Z512 matrix, 2 Nex, 8.8 TE, 600TR |
| STIR Coronal | FSE-XL, 16 FoV, 3 mm slice thickness, 0.5 mm slice gap, 256 × 192 × Z512 matrix, 3 Nex, 60 TE, 4500 TR, 150 IR |

As determined by independent analysis by two certified radiologists blinded to the treatment groups, animals treated with the test composition comprising a rhPDGF-BB solution combined with a β-TCP/type I collagen matrix demonstrated superior healing of the infraspinatus tendon in comparison to animals treated with the control composition.

Subsequent to imaging, all the animals were humanely euthanized by bolus injection of pentobarbital (Euthansol B) 100-200 mg/kg. Necropsy and tissue collection were conducted on each euthanized animal for biomechanical and histological analysis.

Biomechanical Testing

Following sacrifice, the treated and contralateral shoulders of all animals were dissected for biomechanical testing. All dissected shoulders were first wrapped in saline soaked gauze, placed in individual, uniquely identified plastic bags, and frozen to −80° C. until time for testing. During testing, the contralateral shoulders were used to normalize animal to animal variability. Testing was performed using a biomechanical testing apparatus model number 150 kN from Instron of Norwood, Mass., in which the free tendon was affixed with a cryo-clamp. The humeral head was affixed by means of an intramedullary bolt passed through the humeral head in a clevis device arrangement. The tendon and humerus were then distracted at a rate of 4 mm/second until complete separation of the tendon and humerus was achieved. The force was recorded at 0.02 second increments. Mode of failure was also recorded. Table 4 summarizes the results of the biomechanical testing for each animal in the study.

TABLE 4

Summary of biomechanical testing results

| Specimen | Treatment | File Name | Max Load (N) | Mode of Failure | Mean Force to Failure (N) |
|---|---|---|---|---|---|
| Contralateral Control | G2051R | Pull01d | 1313 | Avulsion | 1269 |

TABLE 4-continued

Summary of biomechanical testing results

| Specimen | Treatment | File Name | Max Load (N) | Mode of Failure | Mean Force to Failure (N) |
|---|---|---|---|---|---|
| Contralateral Control | G1627R | Pull02 | 1108 | Avulsion | |
| Contralateral Control | G2054r | Pull05a | 694 | Tendon Tear | |
| Contralateral Control | G1636L | Pull08 | 1503 | Bone Fracture | |
| Contralateral Control | G2437L | Pull09 | 1069 | Avulsion | |
| Contralateral Control | G2923R | Pull12 | 1929 | Bone Fracture | |
| Matrix | G2054L | Pull04 | 367 | Tendon Tear | 543 |
| Matrix | G2923L | Pull10 | 625 | Tendon Tear | |
| Matrix | G2437R | Pull11 | 636 | Tendon Tear | |
| PDGF | G1627L | Pull03 | 1179 | Avulsion | 994 |
| PDGF | G1636R | Pull06 | 960 | Avulsion | |
| PDGF | G2051L | Pull07 | 845 | Avulsion | |

By applying a t-test to the above data to compare control composition versus test composition treated shoulders, a statistically significant (p=0.028) increase in load to failure was observed among animals treated with test composition comprising rhPDGF-BB. Table 5 provides a summary of the statistical analysis.

TABLE 5

Summary of statistical analysis

| Normality Test: | Passed (P = 0.648) | | | |
|---|---|---|---|---|
| Equal Variance Test: | Passed (P = 0.837) | | | |

| Group Name | N | Missing | Mean | Std. Dev. | SEM |
|---|---|---|---|---|---|
| Matrix | 3 | 0 | 550.000 | 152.069 | 87.797 |
| PDGF | 3 | 0 | 994.000 | 169.237 | 97.709 |
| Difference: | | | −444.000 | | |

T = −3.380 with 4 degrees of freedom. (P = 0.028)

The increased load to failure in shoulders treated with the test composition indicated that the test composition comprising PDGF provided a stronger tendon reattachment to the bone in comparison to the control composition.

Additionally, all tendons treated with the test composition exhibited failure at the tendon insertion by avulsion on the bone, whereas tendons treated with the control compositions failed in the midsubstance of the tendon through tearing and delamination. This difference in mode of failure suggests that the application of rhPDGF-BB increases the tensile strength and maturity of the tendon, which does not occur in the control group, resulting in avulsion from the insertion site.

EXAMPLE 6

Treatment of Rotator Cuff Injuries with β-Tricalcium Phosphate/PDGF Compositions This study evaluated the efficacy of a composition comprising a rhPDGF-BB solution combined with a biocompatible type I bovine collagen matrix for the treatment and/or repair of rotator cuff injuries.

Experimental Design

Sheep were selected as an appropriate animal model for the present study. The biomechanical forces measured in the rotator cuff of sheep approximate those which occur in the human shoulder. The animals and protocol used in this study are the current benchmark standard for evaluating rotator cuff repair.

A total of forty (40) animals were studied. All the animals were female and skeletally mature as determined by plain film radiography to ensure closure of the physis. The 40 animals were divided into 5 treatment groups as provided in Table 6 below. All animals were randomly assigned to the treatment groups.

TABLE 6

Summary of animal treatment groups

| Treatment Group | Animals (n) | rhPDGF-BB | Imaging | Endpoint |
|---|---|---|---|---|
| 1 Suture | 8 | 0 | MRI | Biomechanics |
| 2 Matrix + Buffer | 8 | 0 | MRI | Biomechanics |
| 3 Matrix + Dose I | 8 | 0.3 mg/mL | MRI | Biomechanics |
| 4 Matrix + Dose II | 8 | 1.0 mg/mL | MRI | Biomechanics |
| 5 Matrix + Dose III | 8 | 3.0 mg/mL | MRI | Biomechanics |

Animals of all groups underwent two procedures. The first procedure was a resection of the infraspinatus muscle and cutting of the rotator cuff tendon. The second procedure occurred two weeks from the tendon detachment surgery to repair the tendon to bone at its insertion on the humerus. Reattachment of the rotator cuff tendon was administered with bone anchors as provided herein.

Group 1 received only bone anchors and suture for the reattachment of the tendon. In addition to bone anchors and suture, Group 2 received a type I collagen matrix hydrated with sodium acetate buffer (20 mM Na Acetate, pH 6.0), the hydrated collagen matrix positioned at the site of tendon reattachment. Moreover, in addition to bone anchors and suture, Groups 3, 4, and 5 received a type I collagen matrix hydrated with a rhPDGF-BB solution (0.3 mg/mL, 1.0 mg/mL, and 3.0 mg/mL, respectively), the hydrated collagen matrix positioned at the site of tendon reattachment. Collagen matrices hydrated and applied to animals in Groups 2-5 were obtained and are commercially available from Kensey Nash Corporation of Exton, Pa. under the tradename BIO-BLANKET®.

Surgical Protocol

All animals were determined to be Q-fever negative prior to being placed in this study. Food was withheld from each animal 24 to 48 hours prior to the procedures and water was removed the morning of surgery. Each animal was given a general health evaluation (subject to visual observation for attitude, activity, and ease in respiration, freedom for diarrhea and nasal discharge) prior to being placed on the study. Respiratory infection, temperature elevations, observed depression, lameness or anatomical abnormality resulted in rejection of an individual animal from the surgical procedure. Each animal was weighed within 7 days prior to the procedure. Blood was collected for a CBC and Chemistry Profile within 7 days of surgery.

Acepromazine maleate 0.05 mg/kg and Buprenorphine 0.005-0.01 mg/kg were administered im prior to anesthetic induction. An intravenous injection consisting of Diazepam 0.22 mg/kg and Ketamine 10 mg/kg was given for induction of general anesthesia. A cuffed endotracheal tube was placed and general anesthesia maintained with Isoflurane 0.5-5% delivered in oxygen through a rebreathing system. Each animal was placed on a ventilator to assist respiration. A catheter was placed in a peripheral ear vein of each animal. A stomach tube was placed if regurgitation occurred.

All surgical procedures were conducted utilizing routine aseptic techniques. Pre-operative preparation was conducted in the animal preparation room adjacent to the operating room. The appropriate shoulder and surrounding areas of each animal were prepared by clipping the area. Each animal was then moved to the operating room, and the area cleansed with chlorhexidine scrub alternating with 70% isopropyl alcohol three times and painted with iodine solution. Each animal was then draped for sterile surgery. Lactated Ringer's Solution (LRS) was intravenously infused at a rate of approximately 10-20 ml/kg/hr during surgery. Cefazolin 1-2 g was intravenously administered prior to the initial incision and 0.5 g Cefazolin was placed in the flush solution for every surgery.

A. Tendon Detachment Surgical Procedure

A 15 cm curved incision was made over the posterolateral aspect of the shoulder joint. The incision was deepened, and the acromial portion of the deltoid muscle was identified. The muscle was elevated at its cranial edge to expose the tendinous insertion of the infraspinatus muscle and its insertion into the proximal part of the humerus bone. The infraspinatus tendon was detached sharply from its insertion on the proximal humerus. The tendon was then wrapped in a sheet of PRECLUDE®. This allowed diffusion of nutrients to the tendon but inhibited scarring of the tendon to the surrounding tissues. The incision was closed in standard fashion. A 10 cm diameter softball was affixed to the hoof of the limb associated with the operation to inhibit weight bearing for 7 weeks post-operation. Cefazolin 1g was administered iv. A 100 μg fentanyl patch was placed on the animal.

B. Tendon Reattachment Surgical Procedure

Figure 4:
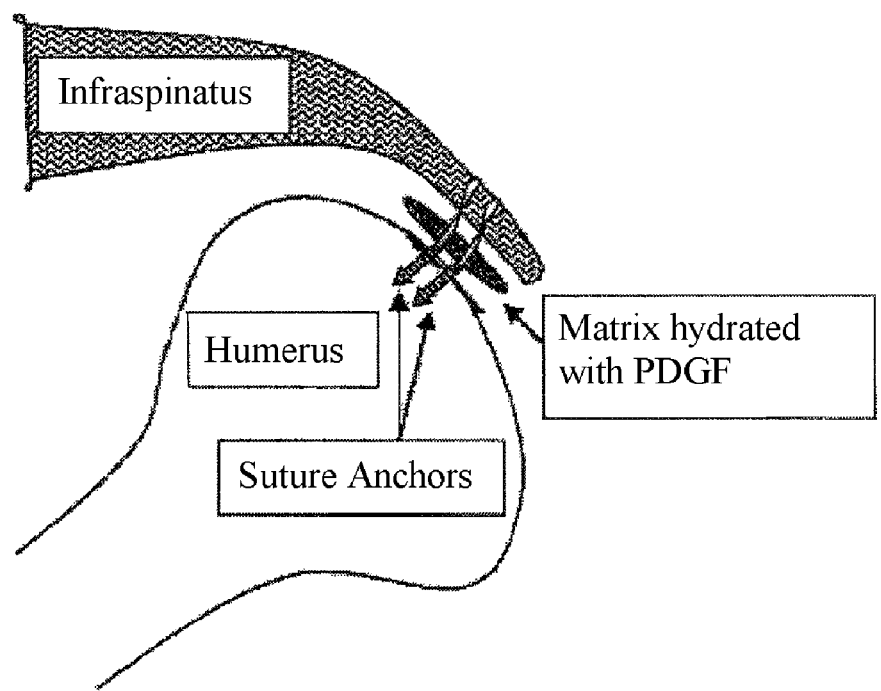
FIG. 4 illustrates a surgical procedure according to one embodiment of the present invention.

Two weeks following the tendon detachment surgery the animals were shaved and prepped for surgery. General anesthesia was administered to each animal as provided hereinabove. The shoulder was approached as described previously. The surface of the tuberosity was roughened with a rongeur to create a bleeding bone surface prior to anchor insertion. Two metal suture anchors were used, typically 6 mm in length by 2-3 mm wide (commercially available from Smith and Nephew Endoscopy of Andover, Mass.). Each anchor was screwed in within the boundary of the footprint until flush with the humeral surface. The center of both anchors were placed approximately 1 cm apart. The tendon was unwrapped and mobilized by blunt dissection. For animals receiving a type I collagen patch hydrated with acetate buffer or a rhPDGF-BB solution, a No. 2 ETHIBOND® braided polyester suture (Johnson and Johnson) looped through the anchors was first passed through the collagen patch, passed through the tendon, tied with a modified Mason-Allen knot, and pulled over the tendon footprint. The tendon was permanently tied to the anchor and the wound is closed in a standard fashion. FIG. 4 illustrates positioning of the collagen patch at the site of tendon reattachment.

Prior to implantation and to facilitate handling and placement, each collagen patch was cut in half using a sterile ruler and scalpel to create two (2) 1 cm² collagen patches. Subsequent to cutting and prior to implantation, each 1 cm² collagen patch was hydrated by application of 150 μL of acetate buffer or rhPDGF-BB solution for 5 minutes until completely saturated. As provided herein, all animals that received the type I collagen patch have sutures from each anchor passed through each 1 cm² patch with a needle driver, and the patch pushed along the sutures until it is positioned over the decorticated footprint.

The tissue layers of each animal were subsequently closed, the edges of the skin incision re-apposed, sutured, and stapled. Each animal received a post-operative analgesic to minimize pain. The operated limb had a softball placed under the hoof during this post-operative period, which allowed limited movement for five weeks. Five (5) weeks following the reattachment procedure, all animals were imaged by MRI, and the scans are assessed by a radiologist. At the time of MRI, the softballs and casts were removed. The following week, six (6) weeks post-reattachment, all animals were humanely sacrificed, and the rotator cuff and attached infraspinatus tendon collected for biomechanical testing.

In Vivo Observations and Measurements

Clinical Observations

Animals were observed daily until the terminal procedure. During the first 14 days post-operatively, the animals were observed for general attitude, appetite, urine/fecal production, appearance of the surgical site and respirator stress. Temperature, pulse and heart rate were recorded for the first 3 days post-operatively. Pain was assessed for a minimum of 7 days post-operatively according to the Evaluation Form for the Assessment of Pain in Sheep and Goats. Antibiotics were administered to an animal if infection developed at the surgical site and was noted in the observations. Body weights were recorded prior to each surgical procedure and before the terminal procedure. Food consumption was qualitative. Animals were monitored daily and the degree of appetite is recorded.

MRI Imaging

MRI scans were taken of each animal at the direction of the study sponsor. Each animal was sedated and then placed in a lateral decubitus position with the operated shoulder down. Each animal was restrained to the table, monitored, and scanned for approximately 20 minutes. Table 7 provides MRI sequence protocols. After scanning, each animal was revived. Scans are forwarded to designated radiologists for a blind review.

TABLE 7

MRI sequence protocols

| | Sagittal PD | | Sagittal T1 |
|---|---|---|---|
| tr | 1000 | tr | 500 |
| te | 10 | te | 10 |
| etl | 4 | etl | 2 |
| rbw | 31 | rbw | 25 |
| fov | 14 | fov | 14 |
| slice thick | 4 | slice thick | 4 |
| slice gap | 0 | slice gap | 0 |
| mtrx | 512 × 512 | mtrx | 512 × 512 |
| nex | 3 | nex | 2 |
| pulse seq | fse | pulse seq | fse |

| | Coronal PD Fat/Sat | | Sagittal PD Fat/Sat |
|---|---|---|---|
| tr | 1450 | tr | 1350 |
| te | 11 | te | 11 |
| etl | 4 | etl | 4 |
| rbw | 31 | rbw | 31 |
| fov | 14 | fov | 14 |
| slice thick | 4 | slice thick | 4 |
| slice gap | 0 | slice gap | 0 |
| mtrx | 512 × 512 | mtrx | 512 × 512 |
| nex | 3 | nex | 3 |
| pulse seq | fse | pulse seq | fse |

Necropsy

Eight (8) weeks following the tendon detachment surgery all animals were humanely sacrificed for tissue collection.

The humerus and approximately four (4) inches of the humeral shaft were collected along with the attached infraspinatus tendon and approximately two (2) inches of muscle distal to the myotendinous junction. All tissues were promptly wrapped in saline soaked gauze, double wrapped in labeled sealed plastic bags, and frozen to −20° C. until they were thawed for biomechanical testing.

Biomechanical Testing

Biomechanical testing was performed by the Rhode Island Hospital Orthopedic Foundation, Inc. During biomechanical testing, contralateral shoulders of the animals were used to normalize animal to animal variability. Testing was performed using an biomechanical testing apparatus model number 150 kN from Instron of Norwood, Mass., in which the free tendon was affixed with a cryo-clamp. The humeral head was affixed by means of an intramedullary bolt passed through the humeral head in a clevis device arrangement. The tendon and humerus were then distracted at a rate of 4 mm/second until complete separation of the tendon and humerus was achieved. The force was recorded at 0.02 second increments. Mode of failure was also recorded.

Shoulders treated with a type I collagen patch saturated with a rhPDGF-BB solution demonstrated an improvement in the ultimate force to tendon separation from the shoulder. Table 8 summarizes the force required to separate the reattached tendon from the shoulder as a percentage of the force required to separate the normal contralateral from its insertion into the humerus.

TABLE 8

Summary of Biomechanical Testing

| Group | % of Normal |
| --- | --- |
| 1 (Suture only) | 59.6 |
| 3 (Matrix, 0.3 mg/ml PDGF) | 79.8 |
| 4 (Matrix, 1.0 mg/ml PDGF) | 75.3 |
| 5 (Matrix, 3.0 mg/ml PDGF) | 73.5 |

As displayed in Table 8, force to tendon separation was higher for shoulders treated with a type I collagen patch saturated with a rhPDGF-BB solution indicating a stronger reattachment of the tendon to the bone in comparison with suture only.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A method of treating a damaged or injured tendon in an individual comprising:
   a) providing a composition consisting of a PDGF solution disposed in a biocompatible matrix,
      wherein the biocompatible matrix is selected from the group consisting of: a biocompatible matrix consisting of collagen, and a biocompatible matrix consisting of collagen and a polysaccharide,
      wherein the PDGF solution consists of PDGF in a buffer,
      wherein the PDGF solution has a concentration of PDGF of about 0.05 mg/ml to about 5 mg/ml, and
      wherein the biocompatible matrix has a porosity greater than about 25%, and
   b) applying the composition in vivo to the damaged or injured tendon.

2. The method of claim 1, wherein the at least one tendon has tearing, delamination, strain, deformation, or combinations thereof.

3. The method of claim 1, wherein the method is a method for attaching the tendon to a bone, and wherein the composition is applied to at least one site of tendon attachment on the bone.

4. The method of claim 3, wherein the method comprises treating a rotator cuff tear, wherein the bone is a humeral head.

5. The method of claim 4, wherein the at least one site of tendon attachment comprises a channel in cortical bone of the humeral head.

6. The method of claim 5, wherein the channel comprises a size and a shape that corresponds to a tendon attachment footprint.

7. The method of claim 4, further comprising disposing at least one bone anchor in the humeral head and coupling at least one detached tendon to the bone anchor.

8. The method of claim 7, wherein the at least one bone anchor comprises PDGF and a second biocompatible matrix.

9. The method of claim 7, wherein the at least one tendon is coupled to the at least one bone anchor through at least one suture.

10. The method of claim 9, wherein the at least one suture is coated with PDGF.

11. The method of claim 7, wherein the composition is positioned between the humeral head and the tendon.

12. The method of claim 4, further comprising molding the composition to contours of the tendon attachment site.

13. The method of claim 4, wherein applying the composition comprises injecting the composition at the tendon reattachment site.

14. The method of claim 1, wherein the method is a method of strengthening the attachment of the tendon to a bone, and wherein the composition is applied to a site of tendon attachment to the bone.

15. The method of claim 1, wherein the biocompatible matrix consists of collagen.

16. The method of claim 15, wherein the biocompatible matrix is a collagen patch or pad.

17. The method of claim 15, wherein the composition is flowable.

18. The method of claim 15, wherein the PDGF solution has a concentration of PDGF ranging from about 0.1 mg/ml to about 1.0 mg/ml.

19. The method of claim 15, wherein the PDGF solution has a concentration of PDGF ranging from about 0.1 mg/ml to about 0.3 mg/ml.

20. The method of claim 15, wherein the PDGF solution has a concentration of PDGF of about 0.15 mg/ml.

21. The method of claim 15, wherein the PDGF solution has a concentration of PDGF of about 0.3 mg/ml.

22. The method of claim 15, wherein the PDGF solution consists of PDGF in a sodium acetate buffer.

23. The method of claim 15, wherein the PDGF is rhPDGF-BB.

24. The method of claim 15, wherein the biocompatible matrix has a porosity greater than about 50%.

25. The method of claim 15, wherein the biocompatible matrix has a porosity greater than about 90%.

26. The method of claim 15, wherein the biocompatible matrix is resorbed within 1 month of in vivo application.

27. The method of claim 15, wherein the biocompatible matrix provides a framework suitable for bone and tendon tissue in-growth.

28. The method of claim 15, wherein the biocompatible matrix is a collagen pad or patch, wherein the PDGF solution has a concentration of PDGF ranging from about 0.1 mg/ml to about 1.0 mg/ml, and wherein the biocompatible matrix has a porosity greater than about 50%.

29. The method of claim 28, wherein the method is a method for attaching the tendon to a bone, and wherein the composition is applied to at least one site of tendon attachment on the bone.

30. The method of claim 15, wherein the biocompatible matrix is a collagen pad or patch, wherein the PDGF solution has a concentration of PDGF ranging from about 0.1 mg/ml to about 0.3 mg/ml, wherein the PDGF solution consists of PDGF in a sodium acetate buffer, wherein the biocompatible matrix has a porosity greater than about 50%, and wherein the biocompatible matrix is resorbed within 1 month of in vivo application.

31. The method of claim 15, wherein the at least one tendon has tearing, delamination, strain, deformation, or combinations thereof.

32. The method of claim 15, wherein the method is a method for attaching the tendon to a bone, and wherein the composition is applied to at least one site of tendon attachment on the bone.

33. The method of claim 15, wherein the method is a method of strengthening the attachment of the tendon to a bone, and wherein the composition is applied to a site of tendon attachment to the bone.

34. The method of claim 15, wherein the biocompatible matrix is resorbed with 3 months of in vivo application.

35. The method of claim 15, wherein the PDGF is recombinant human PDGF.

36. The method of claim 15, wherein the PDGF is PDGF-BB.

37. The method of claim 15, wherein the collagen is type I collagen.

* * * * *